US009802917B2

(12) United States Patent
Buschmann et al.

(10) Patent No.: US 9,802,917 B2
(45) Date of Patent: Oct. 31, 2017

(54) PARTICLES OF N-(5-CYANO-4-((2-METHOXYETHYL) AMINO)PYRIDIN-2-YL)-7-FORMYL-6-((4-METHYL-2-OXOPIPERAZIN-1-YL) METHYL)-3,4-DIHYDRO-1,8-NAPHTHYRIDINE-1(2H)-CARBOXAMIDE

(71) Applicants: Nicole Buschmann, Basel (CH); Robin Alec Fairhurst, Allschwil (CH); Pascal Furet, Thann (FR); Bo Han, Shanghai (CN); Thomas Knöpfel, Rheinfelden (CH); Catherine Leblanc, Basel (CH); Lv Liao, Shanghai (CN); Robert Mah, Muttenz (CH); Franck Mallet, Basel (CH); Julie Martz, Colmar (FR); Can Wang, Suzhou (CN); Jing Xiong, Shanghai (CN); Xianglin Zhao, Shanghai (CN)

(72) Inventors: Nicole Buschmann, Basel (CH); Robin Alec Fairhurst, Allschwil (CH); Pascal Furet, Thann (FR); Bo Han, Shanghai (CN); Thomas Knöpfel, Rheinfelden (CH); Catherine Leblanc, Basel (CH); Lv Liao, Shanghai (CN); Robert Mah, Muttenz (CH); Franck Mallet, Basel (CH); Julie Martz, Colmar (FR); Can Wang, Suzhou (CN); Jing Xiong, Shanghai (CN); Xianglin Zhao, Shanghai (CN)

(73) Assignee: Novartis AG, Basel (CH)

( * ) Notice: Subject to any disclaimer, the term of this patent is extended or adjusted under 35 U.S.C. 154(b) by 0 days.

(21) Appl. No.: 15/073,766

(22) Filed: Mar. 18, 2016

(65) Prior Publication Data
US 2016/0304489 A1    Oct. 20, 2016

(30) Foreign Application Priority Data
Mar. 25, 2015 (WO) ............... PCT/CN2015/000202

(51) Int. Cl.
| A61K 31/496 | (2006.01) |
| C07D 471/04 | (2006.01) |
| C07D 401/14 | (2006.01) |
| C07C 51/41 | (2006.01) |
| C07C 59/265 | (2006.01) |

(52) U.S. Cl.
CPC .......... *C07D 401/14* (2013.01); *C07C 51/412* (2013.01); *C07C 59/265* (2013.01); *C07D 471/04* (2013.01); *C07B 2200/13* (2013.01)

(58) Field of Classification Search
CPC ............. A61K 31/496; C07D 471/04
USPC ................... 514/253.04; 544/362
See application file for complete search history.

(56) References Cited

U.S. PATENT DOCUMENTS

| 2008/0287445 A1 | 11/2008 | Coats et al. |
| 2011/0172217 A1 | 7/2011 | Fujioka et al. |
| 2012/0252780 A1 | 10/2012 | Ng et al. |
| 2016/0102092 A1 | 4/2016 | Buschmann et al. |

FOREIGN PATENT DOCUMENTS

| CN | 1284944 A | 2/2001 |
| CN | 101405002 A | 4/2009 |
| CN | 102725291 A | 10/2012 |
| EP | 1 475 368 A1 | 11/2004 |
| EP | 1 541 563 A1 | 6/2005 |
| EP | 1 604 981 A1 | 12/2005 |
| EP | 1 995 246 A1 | 11/2008 |
| WO | 9611930 A1 | 4/1996 |
| WO | 98/04554 A1 | 2/1998 |
| WO | 99/31061 A1 | 6/1999 |
| WO | 99/41239 A1 | 8/1999 |
| WO | 01/21577 A2 | 3/2001 |
| WO | 03/068753 A1 | 8/2003 |
| WO | 2004/056820 A1 | 7/2004 |
| WO | 2004/091485 A2 | 10/2004 |
| WO | 2005/023761 A2 | 3/2005 |
| WO | 2007/009883 A1 | 1/2007 |
| WO | 2007/071752 A2 | 6/2007 |
| WO | 2007/146230 A2 | 12/2007 |
| WO | 2008/112509 A1 | 9/2008 |
| WO | 2009/079008 A1 | 6/2009 |
| WO | 2010/027002 A1 | 3/2010 |
| WO | 2010/080478 A1 | 7/2010 |
| WO | 2010119284 A1 | 10/2010 |
| WO | 2010/129467 A1 | 11/2010 |
| WO | 2011/051425 A1 | 5/2011 |
| WO | 2011/059839 A1 | 5/2011 |
| WO | 2011/093501 A1 | 8/2011 |
| WO | 2011/111880 A1 | 9/2011 |
| WO | 2012/016217 A1 | 2/2012 |
| WO | 2012/127385 A1 | 9/2012 |
| WO | 2013061080 A1 | 5/2013 |
| WO | 2014/011900 A2 | 1/2014 |
| WO | 2014059202 A1 | 4/2014 |
| WO | 2014059214 A1 | 4/2014 |
| WO | 2014079709 A1 | 5/2014 |

(Continued)

OTHER PUBLICATIONS

French et al., Targeting FGFR4 Inhibits Hepatocellular Carcinoma in Preclinical Mouse Models. PLoS One. May 2012;7(5):1-12.
Mellor, Targeted inhibition of the FGF19-FGFR4 pathway in hepatocellular carcinoma; translational safety considerations. Liver Int. Jul. 2014;34(6):e1-9.
Hubbard et al., Evidence for a common mechanism of SIRT1 regulation by allosteric activators. Science. Mar. 8, 2013;339(6124):1216-9.

(Continued)

*Primary Examiner* — Brenda Coleman
(74) *Attorney, Agent, or Firm* — Gregory Houghton

(57) ABSTRACT

The present invention relates to particles of N-(5-cyano-4-((2-methoxyethyl)amino)pyridin-2-yl)-7-formyl-6-((4-methyl-2-oxopiperazin-1-yl)methyl)-3,4-dihydro-1,8-naphthyridine-1(2H)-carboxamide, to a process of making said particles, to pharmaceutical compositions comprising said particles and to method of treating cancers using said pharmaceutical compositions.

15 Claims, 11 Drawing Sheets

(56) References Cited

FOREIGN PATENT DOCUMENTS

| WO | 2014/144737 A1 | 9/2014 |
| WO | 2014/174307 A1 | 10/2014 |
| WO | 2014172644 A2 | 10/2014 |
| WO | 2015/006492 A1 | 1/2015 |
| WO | 2015030021 A1 | 3/2015 |
| WO | 2015057963 A1 | 4/2015 |
| WO | 2015059668 A1 | 4/2015 |
| WO | 2015061572 A1 | 4/2015 |

OTHER PUBLICATIONS

Zhou W. et al.; A Structure-Guided Approach to Creating Covalent FGFR Inhibitors. Chemistry and Biology. Mar. 26, 2010; 17 (3); 285-295.

Repana, D. et al; Targeting FGF19/FGFR4 Pathway: A Novel Therapeutic Strategy for Hepatocellular Carcinoma. Diseases. Oct. 28, 2015; 3; 294-305.

Figure 6 – Distribution density

Figure 7 – Distribution density

PARTICLES OF
N-(5-CYANO-4-((2-METHOXYETHYL)AMINO)
PYRIDIN-2-YL)-7-FORMYL-6-((4-METHYL-
2-OXOPIPERAZIN-1-YL)METHYL)-3,4-
DIHYDRO-1,8-NAPHTHYRIDINE-1(2H)-
CARBOXAMIDE

FIELD OF THE INVENTION

The present invention relates to particles of N-(5-cyano-4-((2-methoxyethyl)amino)pyridin-2-yl)-7-formyl-6-((4-methyl-2-oxopiperazin-1-yl)methyl)-3,4-dihydro-1,8-naphthyridine-1(2H)-carboxamide, to a process of making said particles and the use of said particles in pharmaceutical compositions.

BACKGROUND OF THE INVENTION

N-(5-cyano-4-((2-methoxyethyl)amino)pyridin-2-yl)-7-formyl-6-((4-methyl-2-oxopiperazin-1-yl)methyl)-3,4-dihydro-1,8-naphthyridine-1(2H)-carboxamide is a selective and potent FGFR4 inhibitor which is described in patent application PCT/IB2014/065585. It is potentially useful in the treatment of diseases mediated by FGFR4, such as cancer, in particular such as liver cancer. PCT/IB2014/065585 describes a method of making N-(5-cyano-4-((2-methoxyethyl)amino)pyridin-2-yl)-7-formyl-6-((4-methyl-2-oxopiperazin-1-yl)methyl)-3,4-dihydro-1,8-naphthyridine-1(2H)-carboxamide in free form and in pharmaceutically acceptable salt form.

There is a continuing need during drug development to develop new processes aimed at improving the properties and/or characteristics of a drug substance. For example, the drug substance should be in a form which is easy to handle and to process into a drug product. Such ideal properties of a drug substance should be achieved by processes which are scalable and reproducible.

SUMMARY OF THE INVENTION

The invention provides particles of N-(5-cyano-4-((2-methoxyethyl)amino)pyridin-2-yl)-7-formyl-6-((4-methyl-2-oxopiperazin-1-yl)methyl)-3,4-dihydro-1,8-naphthyridine-1(2H)-carboxamide in citric acid salt form and a process to make said particles. The particles can be used in the manufacture of pharmaceutical compositions and used in methods for treating, preventing or ameliorating cancers. The process described herein allows making particles of N-(5-cyano-4-((2-methoxyethyl)amino)pyridin-2-yl)-7-formyl-6-((4-methyl-2-oxopiperazin-1-yl)methyl)-3,4-dihydro-1,8-naphthyridine-1(2H)-carboxamide which have beneficial properties in terms of ease of processability. The particles have improved flow properties compared to those obtained by the process described in PCT/IB2014/065585 as shown in more details in the detailed description, the experimental section and the figures provided herein.

Various embodiments of the invention are described herein.

Provided herein is a process for the preparation of particles of N-(5-cyano-4-((2-methoxyethyl)amino)pyridin-2-yl)-7-formyl-6-((4-methyl-2-oxopiperazin-1-yl)methyl)-3,4-dihydro-1,8-naphthyridine-1(2H)-carboxamide in citric acid salt form. The process comprises the steps of:
a. Dissolving N-(5-cyano-4-((2-methoxyethyl)amino)pyridin-2-yl)-7-formyl-6-((4-methyl-2-oxopiperazin-1-yl)methyl)-3,4-dihydro-1,8-naphthyridine-1(2H)-carboxamide in propionic acid;
b. Adding citric acid to the solution obtained in step a) to obtain a suspension comprising N-(5-cyano-4-((2-methoxyethyl)amino)pyridin-2-yl)-7-formyl-6-((4-methyl-2-oxopiperazin-1-yl)methyl)-3,4-dihydro-1,8-naphthyridine-1(2H)-carboxamide in citric acid salt form; and
c. Isolating the particles of N-(5-cyano-4-((2-methoxyethyl)amino)pyridin-2-yl)-7-formyl-6-((4-methyl-2-oxopiperazin-1-yl)methyl)-3,4-dihydro-1,8-naphthyridine-1(2H)-carboxamide in citric acid salt form from the suspension obtained in step b.

In an embodiment, the invention provides particles of N-(5-cyano-4-((2-methoxyethyl)amino)pyridin-2-yl)-7-formyl-6-((4-methyl-2-oxopiperazin-1-yl)methyl)-3,4-dihydro-1,8-naphthyridine-1(2H)-carboxamide in citric acid salt form obtainable by the process described herein.

Provided herein are also particles of N-(5-cyano-4-((2-methoxyethyl)amino)pyridin-2-yl)-7-formyl-6-((4-methyl-2-oxopiperazin-1-yl)methyl)-3,4-dihydro-1,8-naphthyridine-1(2H)-carboxamide in citric acid salt form having a median particle size (x50) of between 200 and 300 microns.

In another embodiment, the invention provides particles of N-(5-cyano-4-((2-methoxyethyl)amino)pyridin-2-yl)-7-formyl-6-((4-methyl-2-oxopiperazin-1-yl)methyl)-3,4-dihydro-1,8-naphthyridine-1(2H)-carboxamide in citric acid salt form having a particle size distribution x10 of between 5 and 10 microns.

In another embodiment, the invention provides particles of N-(5-cyano-4-((2-methoxyethyl)amino)pyridin-2-yl)-7-formyl-6-((4-methyl-2-oxopiperazin-1-yl)methyl)-3,4-dihydro-1,8-naphthyridine-1(2H)-carboxamide in citric acid salt form having a particle size distribution x90 of between 400 and 500 microns.

In another embodiment, the invention provides primary particles of N-(5-cyano-4-((2-methoxyethyl)amino)pyridin-2-yl)-7-formyl-6-((4-methyl-2-oxopiperazin-1-yl)methyl)-3,4-dihydro-1,8-naphthyridine-1(2H)-carboxamide in citric acid salt form having a particle size distribution x50 of between 10 and 20 microns.

In another embodiment, the invention provides primary particles of N-(5-cyano-4-((2-methoxyethyl)amino)pyridin-2-yl)-7-formyl-6-((4-methyl-2-oxopiperazin-1-yl)methyl)-3,4-dihydro-1,8-naphthyridine-1(2H)-carboxamide in citric acid salt form having a particle size distribution x10 of between 1 and 5 microns.

In another embodiment, the invention provides primary particles of N-(5-cyano-4-((2-methoxyethyl)amino)pyridin-2-yl)-7-formyl-6-((4-methyl-2-oxopiperazin-1-yl)methyl)-3,4-dihydro-1,8-naphthyridine-1(2H)-carboxamide in citric acid salt form having a particle size distribution x90 of between 50 and 70 microns.

In another embodiment, the invention provides crystalline primary particles of N-(5-cyano-4-((2-methoxyethyl)amino)pyridin-2-yl)-7-formyl-6-((4-methyl-2-oxopiperazin-1-yl)methyl)-3,4-dihydro-1,8-naphthyridine-1(2H)-carboxamide in citric acid salt form having a columnar crystal shape.

In another embodiment, the invention provides an agglomerate comprising primary particles of N-(5-cyano-4-((2-methoxyethyl)amino)pyridin-2-yl)-7-formyl-6-((4-methyl-2-oxopiperazin-1-yl)methyl)-3,4-dihydro-1,8-naphthyridine-1(2H)-carboxamide in citric acid salt form, the agglomerate having a median size (x50) of between 300 and 400 microns.

In another embodiment, the invention relates to the use of particles of N-(5-cyano-4-((2-methoxyethyl)amino)pyridin-2-yl)-7-formyl-6-((4-methyl-2-oxopiperazin-1-yl)methyl)-3,4-dihydro-1,8-naphthyridine-1(2H)-carboxamide in citric acid salt form as described herein in the manufacture of a pharmaceutical composition comprising N-(5-cyano-4-((2-methoxyethyl)amino)pyridin-2-yl)-7-formyl-6-((4-methyl- 2-oxopiperazin-1-yl)methyl)-3,4-dihydro-1,8-naphthyridine-1(2H)-carboxamide in citric acid salt form and optionally one or more pharmaceutically acceptable carrier(s).

In another embodiment, the invention relates to a pharmaceutical composition comprising particles of N-(5-cyano-4-((2-methoxyethyl)amino)pyridin-2-yl)-7-formyl-6-((4-methyl-2-oxopiperazin-1-yl)methyl)-3,4-dihydro-1,8-naphthyridine-1(2H)-carboxamide in citric acid salt form as described herein and optionally one or more pharmaceutically acceptable carrier(s).

In another embodiment, the pharmaceutical composition described herein is for use as a medicament. In a particular embodiment, it is for use in the treatment of cancer. More particularly, it is for use in the treatment of an indication selected from liver cancer, breast cancer, glioblastoma, prostate cancer, rhabdomyosarcoma, gastric cancer, ovarian cancer, lung cancer, colon cancer. Even more particularly, it is for use in the treatment of liver cancer.

In an embodiment, the invention relates to a method of treating cancer comprising administering to a subject a therapeutically effective amount of the pharmaceutical composition as described herein. In an embodiment, the invention relates to the use of a pharmaceutical composition as described herein in the manufacture of a medicament for the treatment of cancer. More particularly, it is for the treatment of an indication selected from liver cancer, breast cancer, glioblastoma, prostate cancer, rhabdomyosarcoma, gastric cancer, ovarian cancer, lung cancer, colon cancer. Even more particularly, it is for the treatment of liver cancer.

DETAILED DESCRIPTION OF THE INVENTION

Definitions

When defining the concentration of a compound in a solution, the term "%" refers to the w/w %, i.e the weight of the compound over the weight of the solution (i.e. compound+solvent).

Unless otherwise defined, the term "particles" in plural as used herein refers to a bulk of particles. Unless otherwise defined, the term "crystals" in plural as used herein refers to a bulk of crystals. The term "particles" is meant to encompass primary particles and agglomerates.

As used herein, the term "primary particle" refers to a singular entity. Primary particles of the invention can be seen for instance in FIGS. 1 and 8.

As used herein, the term "agglomerate" refers to a cluster of primary particles. As used herein, the term "agglomerate" is not intended to be limiting as to the nature of the linkages between the primary particles and can be used for example interchangeably with the term "aggregates". Particle size is determined by the cumulative undersize particle size distribution by volume as measured by laser light diffraction. For instance, the median particle size value (x50 or d50) indicates the size under which 50% by weight of the particles in the sample exist. As an example, a x50 value of 10 microns indicates that 50% by weight of the particles have a size below 10 microns.

Similarly a particle size of x10 or d10 indicates the size under which 10% by weight of the particles in the sample exist.

Similarly a particle size of x90 or d90 indicates the size under which 90% by weight of the particles in the sample exist.

It is understood that the particle sizes given herein are subject to variations depending on the apparatus and method used. A skilled person would understand that these values are not absolute values and may vary by about +/−10%.

In the present description, the particle sizes are measured by laser light diffraction. The apparatus used for laser light diffraction is a Sympatec Helos apparatus. Details of the apparatus used and measurements are given in examples 3 and 4.

As used herein, the abbreviation "microns" corresponds to microns.

Figure 1:
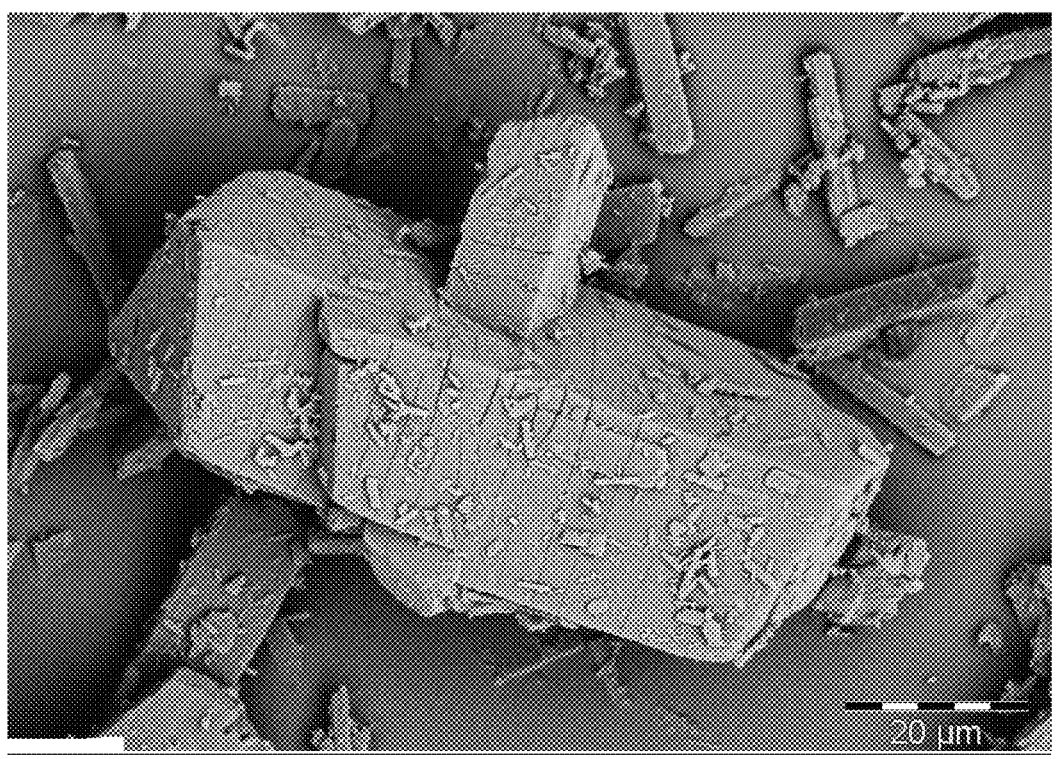
FIG. 1 is a scanning electron microscope (SEM) image of the particles obtained using a process of the invention (scale 20 microns). The image was taken using a SEM apparatus from Zeiss equipped with a Supra 40 microscope. It shows a primary particle having a columnar crystal shape.

As used herein, the term "columnar" when referring to the crystal shape of the particles of the invention describes a crystal shape as shown for example in FIG. 1. A "columnar" crystal shape is a faceted tridimensional growth crystal. A columnar crystal shape can also be defined as a lath. It is distinguishable from a needle crystal shape (or acicular crystal) where the crystal growth is unidirectional.

As used herein, the term "pharmaceutically acceptable carrier" includes any and all solvents, dispersion media, coatings, surfactants, antioxidants, preservatives (e.g., antibacterial agents, antifungal agents), isotonic agents, absorption delaying agents, salts, preservatives, drug stabilizers, binders, excipients, disintegration agents, lubricants, sweetening agents, flavoring agents, dyes, and the like and combinations thereof, as would be known to those skilled in the art (see, for example, Remington's Pharmaceutical Sciences, 18th Ed. Mack Printing Company, 1990, pp. 1289-1329). Except insofar as any conventional carrier is incompatible with the active ingredient, its use in the therapeutic or pharmaceutical compositions is contemplated.

The term "a therapeutically effective amount" of a compound of the present invention refers to an amount of the compound of the present invention that will elicit the biological or medical response of a subject, for example, reduction or inhibition of an enzyme or a protein activity, or ameliorate symptoms, alleviate conditions, slow or delay disease progression, or prevent a disease, etc. In one non-limiting embodiment, the term "a therapeutically effective amount" refers to the amount of the compound of the present invention that, when administered to a subject, is effective to (1) at least partially alleviate, inhibit, prevent and/or ameliorate a condition, or a disorder or a disease (i) mediated by FGFR4, or (ii) associated with FGFR4 activity, or (iii) characterized by activity (normal or abnormal) of FGFR4, or (2) reduce or inhibit the activity of FGFR4; or (3) reduce or inhibit the expression of FGFR4. In another non-limiting embodiment, the term "a therapeutically effective amount" refers to the amount of the compound of the present invention that, when administered to a cell, or a tissue, or a non-cellular biological material, or a medium, is effective to at least partially reduce or inhibit the activity of FGFR4.

As used herein, the term "subject" refers to an animal. Typically the animal is a mammal. A subject also refers to for example, primates (e.g., humans, male or female), cows, sheep, goats, horses, dogs, cats, rabbits, rats, mice, fish, birds and the like. In certain embodiments, the subject is a primate. In yet other embodiments, the subject is a human.

As used herein, the term "inhibit", "inhibition" or "inhibiting" refers to the reduction or suppression of a given condition, symptom, or disorder, or disease, or a significant decrease in the baseline activity of a biological activity or process.

As used herein, the term "treat", "treating" or "treatment" of any disease or disorder refers in one embodiment, to ameliorating the disease or disorder (i.e., slowing or arresting or reducing the development of the disease or at least one of the clinical symptoms thereof). In another embodiment "treat", "treating" or "treatment" refers to alleviating or ameliorating at least one physical parameter including those which may not be discernible by the patient. In yet another embodiment, "treat", "treating" or "treatment" refers to modulating the disease or disorder, either physically, (e.g., stabilization of a discernible symptom), physiologically, (e.g., stabilization of a physical parameter), or both. In yet another embodiment, "treat", "treating" or "treatment" refers to preventing or delaying the onset or development or progression of the disease or disorder.

As used herein, a subject is "in need of" a treatment if such subject would benefit biologically, medically or in quality of life from such treatment.

As used herein, the term "a," "an," "the" and similar terms used in the context of the present invention (especially in the context of the claims) are to be construed to cover both the singular and plural unless otherwise indicated herein or clearly contradicted by the context.

The invention relates to a process for the preparation of particles of N-(5-cyano-4-((2-methoxyethyl)amino)pyridin-2-yl)-7-formyl-6-((4-methyl-2-oxopiperazin-1-yl)methyl)-3,4-dihydro-1,8-naphthyridine-1(2H)-carboxamide in citric acid salt form. N-(5-cyano-4-((2-methoxyethyl)amino)pyridin-2-yl)-7-formyl-6-((4-methyl-2-oxopiperazin-1-yl)methyl)-3,4-dihydro-1,8-naphthyridine-1(2H)-carboxamide in citric acid salt form has the following structure:

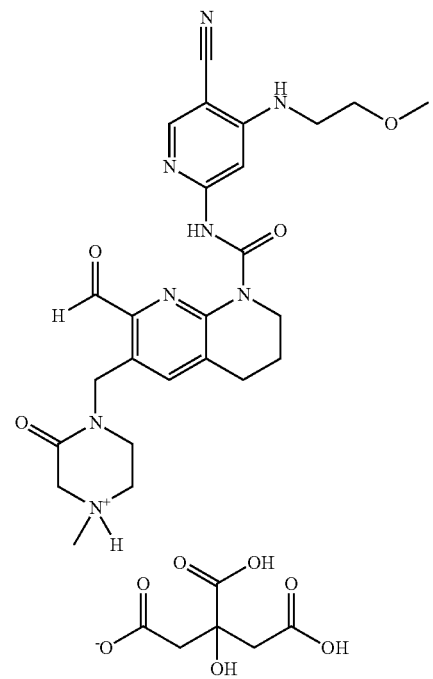

The process comprises step a) dissolving N-(5-cyano-4-((2-methoxyethyl)amino)pyridin-2-yl)-7-formyl-6-((4-methyl-2-oxopiperazin-1-yl)methyl)-3,4-dihydro-1,8-naphthyridine-1(2H)-carboxamide in free form in propionic acid. N-(5-cyano-4-((2-methoxyethyl)amino)pyridin-2-yl)-7-formyl-6-((4-methyl-2-oxopiperazin-1-yl)methyl)-3,4-dihydro-1,8-naphthyridine-1(2H)-carboxamide in free form can be obtained by a process described for instance in example 1 (steps 1 to 14). The concentration of N-(5-cyano-4-((2-methoxyethyl)amino)pyridin-2-yl)-7-formyl-6-((4-methyl-2-oxopiperazin-1-yl)methyl)-3,4-dihydro-1,8-naphthyridine-1(2H)-carboxamide in free form in propionic acid may be between 5-15% (by weight), preferably 5-15%. In one embodiment, the concentration of N-(5-cyano-4-((2-methoxyethyl)amino)pyridin-2-yl)-7-formyl-6-((4-methyl-2-oxopiperazin-1-yl)methyl)-3,4-dihydro-1,8-naphthyridine-1(2H)-carboxamide in free form in propionic acid is about 5-10% by weight. In one embodiment, the concentration of N-(5-cyano-4-((2-methoxyethyl)amino)pyridin-2-yl)-7-formyl-6-((4-methyl-2-oxopiperazin-1-yl)methyl)-3,4-dihydro-1,8-naphthyridine-1(2H)-carboxamide in free form in propionic acid is about 10-15% by weight. In one embodiment, it is about 12% by weight. In one embodiment, it is about 13% by weight. The propionic acid used in the present process is preferably neat. By "neat" is meant that the propionic acid is at least 99% pure. Preferably, propionic acid is at least 99.5% pure. Typically, the temperature used for dissolving N-(5-cyano-4-((2-methoxyethyl)amino)pyridin-2-yl)-7-formyl-6-((4-methyl-2-oxopiperazin-1-yl)methyl)-3,4-dihydro-1,8-naphthyridine-1(2H)-carboxamide in free form in propionic acid is between 50° C. and 80° C., preferably about 70° C. The time needed for complete dissolution depends on the temperature used. Typically, at about 70° C., the time needed is between 10-30 minutes, preferably about 20 minutes. Complete dissolution can easily be determined by a skilled person, for example by visual inspection.

In step b) of the process of the invention, citric acid is added to the solution obtained in step a). Citric acid may be added as a solid, as a solution or as a suspension. When added as a solution or suspension, the concentration may vary from 1 to 50 w/w %. Typically, it is added as a solution or suspension. The solvent used for the citric acid solution is typically a solvent in which N-(5-cyano-4-((2-methoxyethyl)amino)pyridin-2-yl)-7-formyl-6-((4-methyl-2-oxopiperazin-1-yl)methyl)-3,4-dihydro-1,8-naphthyridine-1(2H)-carboxamide in citric acid salt form is poorly soluble. Such solvent may be for example selected from heptane, methyl tert-butyl ether, n-hexane, ethyl acetate, n-propyl acetate, acetone, acetonitrile, toluene, water or mixtures thereof. In an embodiment, the solvent used for the citric acid solution/suspension is acetone. In an embodiment, the solvent used for the citric acid solution/suspension is ethyl acetate. In an embodiment, citric acid is added to the solution obtained in step a) as a solution in acetone. In an embodiment, the concentration of citric acid in acetone is between 1-50%, preferably between 20-30%, more preferably about 23%. In another embodiment, the concentration of citric acid in acetone is between 1-10%, preferably between 1-5%, more preferably about 2.5%.

In an embodiment, citric acid is added to the solution obtained in step a) as a solution in ethyl acetate. In an embodiment, the concentration of citric acid in ethyl acetate is between 1-10%, preferably 1-5%, more preferably about 1.3%.

The amount of citric acid added during the process depends on the desired stoichiometry of the N-(5-cyano-4-((2-methoxyethyl)amino)pyridin-2-yl)-7-formyl-6-((4-methyl-2-oxopiperazin-1-yl)methyl)-3,4-dihydro-1,8-naphthyridine-1(2H)-carboxamide in citric acid salt form. In a preferred embodiment, the desired stoichiometry of N-(5-cyano-4-((2-methoxyethyl)amino)pyridin-2-yl)-7-formyl-6-((4-methyl-2-oxopiperazin-1-yl)methyl)-3,4-dihydro-1,8-naphthyridine-1(2H)-carboxamide in citric acid salt form is 1:1 (citric acid: N-(5-cyano-4-((2-methoxyethyl)amino)pyridin-2-yl)-7-formyl-6-((4-methyl-2-oxopiperazin-1-yl)methyl)-3,4-dihydro-1,8-naphthyridine-1(2H)-carboxamide). In another embodiment, the desired stoichiometry of N-(5-cyano-4-((2-methoxyethyl)amino)pyridin-2-yl)-7-formyl-6-((4-methyl-2-oxopiperazin-1-yl)methyl)-3,4-dihydro-1,8-naphthyridine-1(2H)-carboxamide in citric acid salt form is 0.5:1 (citric acid: N-(5-cyano-4-((2-methoxyethyl)amino)pyridin-2-yl)-7-formyl-6-((4-methyl-2-oxopiperazin-1-yl)methyl)-3,4-dihydro-1,8-naphthyridine-1(2H)-carboxamide). A skilled artisan is able to determine the amount of citric acid required to obtain the desired stoichiometry. The amount of citric acid required may be added at once or in several aliquots. In an embodiment, citric acid is added at once. In another embodiment, citric acid is added in several aliquots. Each aliquot may vary as to the form or may be the same. For instance, in one aliquot, citric acid may be added in solid form. In another aliquot, citric acid may be added as a solution. In another aliquot, citric acid may be added as a suspension. Each aliquot of citric acid may be of the same concentration or of different concentration. The solvent used for each aliquot of citric acid when added as a solution or a suspension may be the same or different. The aliquots may be added over a period of time between 1 second to 10 hours. The temperature at which the citric acid is added may vary from 20-80° C. Preferably, the temperature at which the citric acid is added is about 55° C. Upon citric acid addition, a suspension comprising N-(5-cyano-4-((2-methoxyethyl)amino)pyridin-2-yl)-7-formyl-6-((4-methyl-2-oxopiperazin-1-yl)methyl)-3,4-dihydro-1,8-naphthyridine-1(2H)-carboxamide in citric acid salt form is formed. In an embodiment, there is an additional step of seeding the suspension obtained in step b) with a seed suspension comprising N-(5-cyano-4-((2-methoxyethyl)amino)pyridin-2-yl)-7-formyl-6-((4-methyl-2-oxopiperazin-1-yl)methyl)-3,4-dihydro-1,8-naphthyridine-1(2H)-carboxamide in citric acid salt form. The seed suspension comprises particles of N-(5-cyano-4-((2-methoxyethyl)amino)pyridin-2-yl)-7-formyl-6-((4-methyl-2-oxopiperazin-1-yl)methyl)-3,4-dihydro-1,8-naphthyridine-1(2H)-carboxamide in citric acid salt form obtained by a process of the invention. Preferably, the particles of N-(5-cyano-4-((2-methoxyethyl)amino)pyridin-2-yl)-7-formyl-6-((4-methyl-2-oxopiperazin-1-yl)methyl)-3,4-dihydro-1,8-naphthyridine-1(2H)-carboxamide in citric acid salt form used in the seed suspension have a stoichiometry of 1:1 (citric acid: N-(5-cyano-4-((2-methoxyethyl)amino)pyridin-2-yl)-7-formyl-6-((4-methyl-2-oxopiperazin-1-yl)methyl)-3,4-dihydro-1,8-naphthyridine-1(2H)-carboxamide). For the seed suspension, the particles of N-(5-cyano-4-((2-methoxyethyl)amino)pyridin-2-yl)-7-formyl-6-((4-methyl-2-oxopiperazin-1-yl)methyl)-3,4-dihydro-1,8-naphthyridine-1(2H)-carboxamide in citric acid salt form are suspended in a solvent such as acetone. The seed suspension may be added between the additions of citric acid aliquots or after the total amount of citric acid required has been added to the reaction mixture. The seed suspension typically comprises about 0.005-5%, preferably 0.01-1% particles of N-(5-cyano-4-((2-methoxyethyl)amino)pyridin-2-yl)-7-formyl-6-((4-methyl-2-oxopiperazin-1-yl)methyl)-3,4-dihydro-1,8-naphthyridine-1(2H)-carboxamide in citric acid salt form obtained by a process of the invention. In an embodiment, the seed suspension comprises 0.5% particles of N-(5-cyano-4-((2-methoxyethyl)amino)pyridin-2-yl)-7-formyl-6-((4-methyl-2-oxopiperazin-1-yl)methyl)-3,4-dihydro-1,8-naphthyridine-1(2H)-carboxamide in citric acid salt form obtained by a process of the invention. The temperature of the seed suspension is typically about 20° C.

Figure 8:
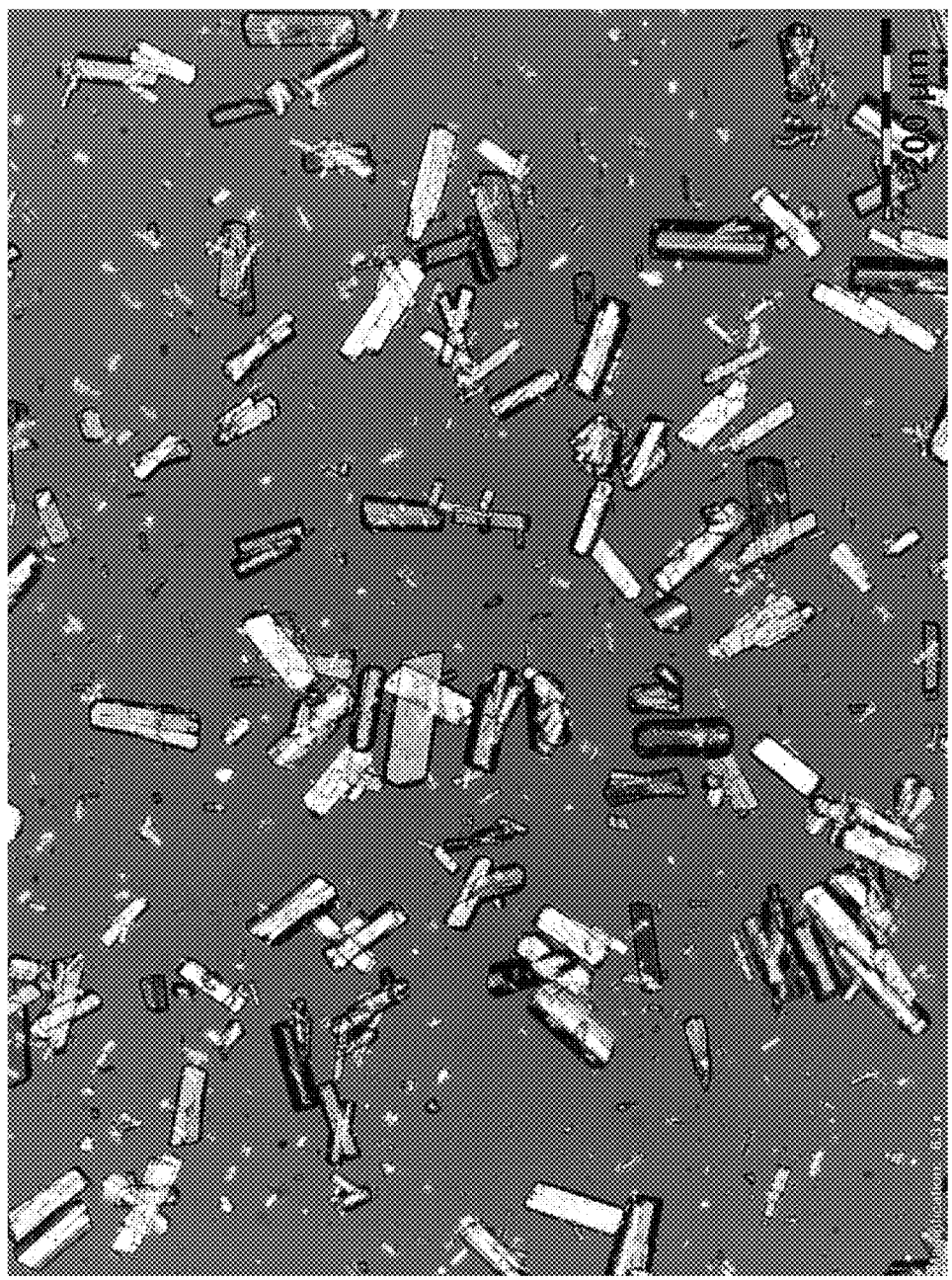
FIG. 8 is the SEM (200 microns) of the particles obtained by the process of the invention steps a) and b), i.e. prior to the isolation step. The image was taken with an Olympus BX51 microscope (serial number SN8G30637) equipped with a camera DP25 (serial number SN8K08782). The software used for imaging is StreamStart. The image shows crystalline particles having a columnar crystal habit.

The suspension obtained in step b) of the process of the invention is typically stirred for a period of time which allows N-(5-cyano-4-((2-methoxyethyl)amino)pyridin-2-yl)-7-formyl-6-((4-methyl-2-oxopiperazin-1-yl)methyl)-3,4-dihydro-1,8-naphthyridine-1(2H)-carboxamide in citric acid salt form to crystallise out of solution. Typically, the suspension may be stirred for 1 minute to 20 hours. The temperature of the resulting suspension may be allowed to drop to about 20° C., if the preceding steps were carried out under temperatures higher than 20° C. FIG. 8 shows a microscope image of the primary particles of N-(5-cyano-4-((2-methoxyethyl)amino)pyridin-2-yl)-7-formyl-6-((4-methyl-2-oxopiperazin-1-yl)methyl)-3,4-dihydro-1,8-naphthyridine-1(2H)-carboxamide in citric acid salt form obtained after step b). In FIG. 8, the primary particles of N-(5-cyano-4-((2-methoxyethyl)amino)pyridin-2-yl)-7-formyl-6-((4-methyl-2-oxopiperazin-1-yl)methyl)-3,4-dihydro-1,8-naphthyridine-1(2H)-carboxamide in citric acid salt form are in suspension in the reaction medium. Step c) in the process of the invention includes isolating the particles of N-(5-cyano-4-((2-methoxyethyl)amino)pyridin-2-yl)-7-formyl-6-((4-methyl-2-oxopiperazin-1-yl)methyl)-3,4-dihydro-1,8-naphthyridine-1(2H)-carboxamide in citric acid salt form from the suspension obtained in the preceding step b). This is typically done by filtration, washing and drying. Thus, in a further embodiment, step c) in the process of the invention includes:

step c1) filtering of the suspension obtained in step b) to give particles of N-(5-cyano-4-((2-methoxyethyl)amino)pyridin-2-yl)-7-formyl-6-((4-methyl-2-oxopiperazin-1-yl)methyl)-3,4-dihydro-1,8-naphthyridine-1(2H)-carboxamide in citric acid salt form;

step c2) washing of the particles obtained after the filtration step c1); and step c3) drying of the particles obtained in step c2).

Filtration may be done using standard techniques and apparatus. For instance, filtration can be done using a glass filter/sinter. Filtration may be done under vacuum, for instance, under 500 mbar. Filtration may be done at room temperature. Filtration may be done under a nitrogen atmosphere.

Washing may be done with one solvent system or with several solvent systems. For instance, in one embodiment, the solvent system used may be a 1:1 mixture of propionic acid and acetone at room temperature. In another embodiment, the solvent system used may also be a 1:1 mixture propionic acid and ethyl acetate at room temperature. In one embodiment, the solvent system used may also be acetone alone at room temperature. In one embodiment, a first washing step is carried out with a 1:1 mixture of propionic acid and acetone at room temperature followed by a second washing step with acetone alone at room temperature. In one embodiment, a first washing step is carried out with a 1:1 mixture of propionic acid and ethyl acetate at room temperature followed by a second washing step with ethyl acetate alone at room temperature.

Typically, drying is carried out using standard techniques. For instance, the resulting particles may be dried in an oven, optionally under vacuum, for instance, under about 5 mbar. Drying may be carried out under a nitrogen atmosphere. Typically, drying is carried out at about 40° C.

The invention covers, in an embodiment, the particles obtainable by a process of the invention described herein.

The particle sizes of the particles of the present invention are measured using laser light diffraction as described in Example 3 and are therefore based on the thus obtained volume weighted particle size distribution. The particle size distribution is represented by a cumulative (undersize) distribution curve (Q3(x) %) and a density distribution curve (q3lg(x)) as is shown for instance in FIG. 6.

Figure 6:
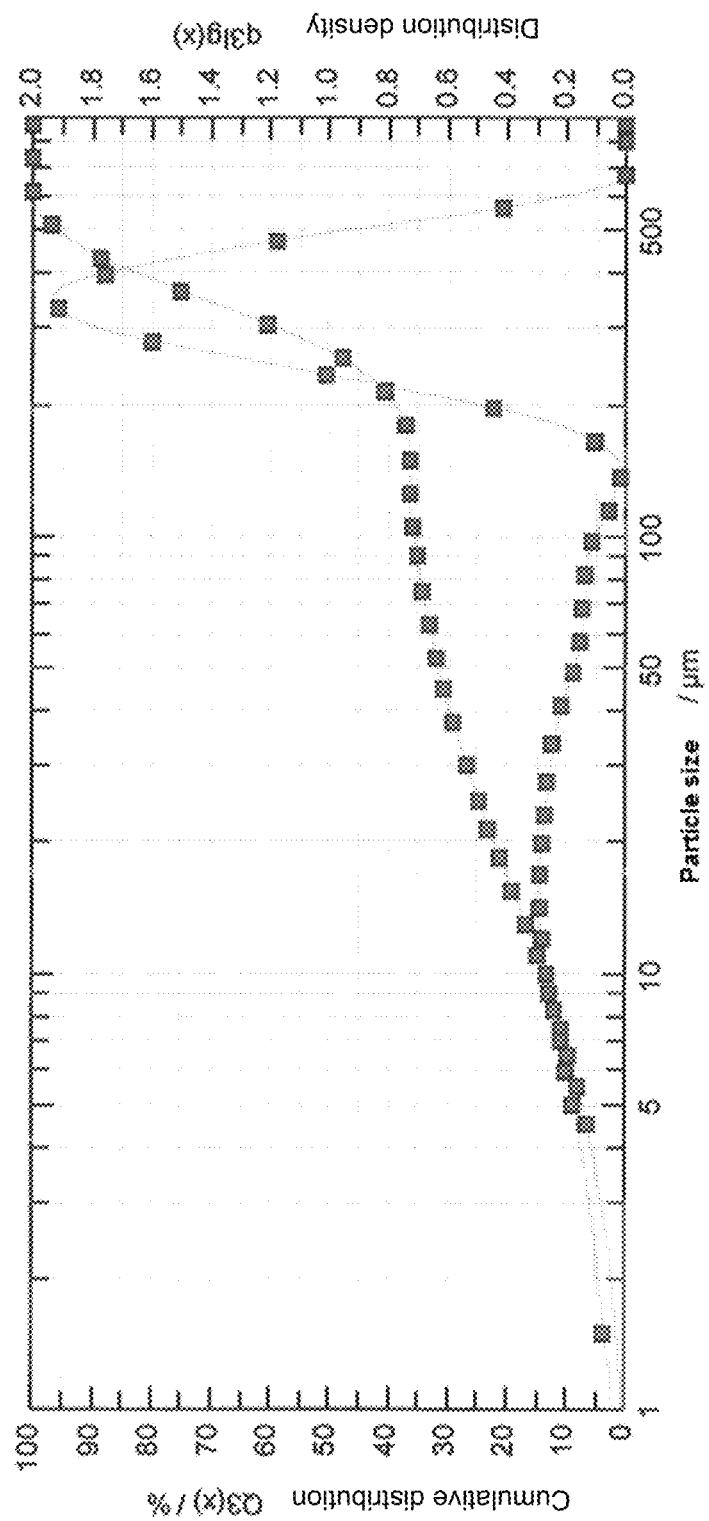
FIG. 6 shows the particle size distribution for particles obtained using the process of the invention. The figure shows the distribution density and the cumulative distribution curves as a function of particle size. It shows that the particles contain a mix of primary particles having a particle size range from 0.5 to 150 microns and agglomerates having a particle size range from 150 to 875 microns.

Thus, in an embodiment, the invention relates to particles of N-(5-cyano-4-((2-methoxyethyl)amino)pyridin-2-yl)-7-formyl-6-((4-methyl-2-oxopiperazin-1-yl)methyl)-3,4-dihydro-1,8-naphthyridine-1(2H)-carboxamide in citric acid salt form having a particle size distribution substantially the same as that shown in FIG. 6. In an embodiment, the invention relates to particles of N-(5-cyano-4-((2-methoxyethyl)amino)pyridin-2-yl)-7-formyl-6-((4-methyl-2-oxopiperazin-1-yl)methyl)-3,4-dihydro-1,8-naphthyridine-1(2H)-carboxamide in citric acid salt form having a cumulative undersize distribution curve substantially the same as that shown in FIG. 6. In an embodiment, the invention relates to particles of N-(5-cyano-4-((2-methoxyethyl)amino)pyridin-2-yl)-7-formyl-6-((4-methyl-2-oxopiperazin-1-yl)methyl)-3,4-dihydro-1,8-naphthyridine-1(2H)-carboxamide in citric acid salt form having a density distribution curve substantially the same as that shown in FIG. 6.

In the present invention, the particle sizes including x10, x50 and x90 values are preferably measured by laser light diffraction.

As can be seen in the particle size distribution graph shown in FIG. 6, the particles obtained using the process of the invention have a cumulative undersize particle size distribution by volume having the following characteristic values:

x10 value of between 5 and 10 microns;
x50 value of between 200 and 300 microns;
x90 value of between 400 and 500 microns.

Thus, in an embodiment, the invention relates to particles of N-(5-cyano-4-((2-methoxyethyl)amino)pyridin-2-yl)-7-formyl-6-((4-methyl-2-oxopiperazin-1-yl)methyl)-3,4-dihydro-1,8-naphthyridine-1(2H)-carboxamide in citric acid salt form having a x10 value of between 5 and 10 microns. Preferably, the particles of N-(5-cyano-4-((2-methoxyethyl)amino)pyridin-2-yl)-7-formyl-6-((4-methyl-2-oxopiperazin-1-yl)methyl)-3,4-dihydro-1,8-naphthyridine-1(2H)-carboxamide in citric acid salt form have a x10 value of about 7 microns. In an embodiment, the x10 value can vary within +/−10%. Thus, in an embodiment, the particles of N-(5-cyano-4-((2-methoxyethyl)amino)pyridin-2-yl)-7-formyl-6-((4-methyl-2-oxopiperazin-1-yl)methyl)-3,4-dihydro-1,8-naphthyridine-1(2H)-carboxamide in citric acid salt form have a x10 value of between 4.5 and 11 microns. As a comparison, N-(5-cyano-4-((2-methoxyethyl)amino)pyridin-2-yl)-7-formyl-6-((4-methyl-2-oxopiperazin-1-yl)methyl)-3,4-dihydro-1,8-naphthyridine-1(2H)-carboxamide in citric acid salt form obtained by the process described in PCT/IB2014/065585 (reference example 1) has a particle size x10 or d10 of about 1 micron (see example 4 and FIG. 7).

In an embodiment, the invention relates to particles of N-(5-cyano-4-((2-methoxyethyl)amino)pyridin-2-yl)-7-formyl-6-((4-methyl-2-oxopiperazin-1-yl)methyl)-3,4-dihydro-1,8-naphthyridine-1(2H)-carboxamide in citric acid salt form having a x50 value of between 200 and 300 microns. Preferably, the particles of N-(5-cyano-4-((2- methoxyethyl)amino)pyridin-2-yl)-7-formyl-6-((4-methyl-2-oxopiperazin-1-yl)methyl)-3,4-dihydro-1,8-naphthyridine-1(2H)-carboxamide in citric acid salt form have a x50 value of about 265 microns. In an embodiment, the x50 value can vary within +/−10%. Thus, in an embodiment, the particles of N-(5-cyano-4-((2-methoxyethyl)amino)pyridin-2-yl)-7-formyl-6-((4-methyl-2-oxopiperazin-1-yl)methyl)-3,4-dihydro-1,8-naphthyridine-1(2H)-carboxamide in citric acid salt form have a x50 value of between 180 and 330 microns. As a comparison, N-(5-cyano-4-((2-methoxyethyl)amino)pyridin-2-yl)-7-formyl-6-((4-methyl-2-oxopiperazin-1-yl)methyl)-3,4-dihydro-1,8-naphthyridine-1(2H)-carboxamide in citric acid salt form obtained by the process described in PCT/IB2014/065585 (reference example 1) has a median particle size (x50 or d50) of about 3 microns (see example 4 and FIG. 7).

In an embodiment, the invention relates to particles of N-(5-cyano-4-((2-methoxyethyl)amino)pyridin-2-yl)-7-formyl-6-((4-methyl-2-oxopiperazin-1-yl)methyl)-3,4-dihydro-1,8-naphthyridine-1(2H)-carboxamide in citric acid salt form having a x90 value of between 400 and 500 microns. Preferably, the particles of N-(5-cyano-4-((2-methoxyethyl)amino)pyridin-2-yl)-7-formyl-6-((4-methyl-2-oxopiperazin-1-yl)methyl)-3,4-dihydro-1,8-naphthyridine-1(2H)-carboxamide in citric acid salt form have a x90 value of about 450 microns. In an embodiment, the x10 value can vary within +/−10%. Thus, in an embodiment, the particles of N-(5-cyano-4-((2-methoxyethyl)amino)pyridin-2-yl)-7-formyl-6-((4-methyl-2-oxopiperazin-1-yl)methyl)-3,4-dihydro-1,8-naphthyridine-1(2H)-carboxamide in citric acid salt form have a x90 value of between 360 and 550 microns. As a comparison, N-(5-cyano-4-((2-methoxyethyl)amino)pyridin-2-yl)-7-formyl-6-((4-methyl-2-oxopiperazin-1-yl)methyl)-3,4-dihydro-1,8-naphthyridine-1(2H)-carboxamide in citric acid salt form obtained by the process described in PCT/IB2014/065585 (reference example 1) has a particle size x90 or d90 of about 7 micron (see example 4 and FIG. 7).

Also, as can be seen from the graph shown in FIG. 6, the particles obtained by the process of the invention can be differentiated into primary particles having a particle size range from 0.5 to 150 microns and agglomerates having a particle size range from 150 to 875 microns.

Thus, in an embodiment, the particles of the invention comprise a mixture of primary particles of N-(5-cyano-4-((2-methoxyethyl)amino)pyridin-2-yl)-7-formyl-6-((4-methyl-2-oxopiperazin-1-yl)methyl)-3,4-dihydro-1,8-naphthyridine-1(2H)-carboxamide in citric acid salt form and agglomerates of primary particles of N-(5-cyano-4-((2-methoxyethyl)amino)pyridin-2-yl)-7-formyl-6-((4-methyl-2-oxopiperazin-1-yl)methyl)-3,4-dihydro-1,8-naphthyridine-1(2H)-carboxamide in citric acid salt form. The primary particles can be separated from the agglomerates by methods known to a person of skill in the art such as sieving for instance.

In an embodiment, the invention therefore relates to primary particles of N-(5-cyano-4-((2-methoxyethyl)amino)pyridin-2-yl)-7-formyl-6-((4-methyl-2-oxopiperazin-1-yl)methyl)-3,4-dihydro-1,8-naphthyridine-1(2H)-carboxamide in citric acid salt form obtainable by a process of the invention described herein.

In an embodiment, the invention relates to primary particles of N-(5-cyano-4-((2-methoxyethyl)amino)pyridin-2-yl)-7-formyl-6-((4-methyl-2-oxopiperazin-1-yl)methyl)-3,4-dihydro-1,8-naphthyridine-1(2H)-carboxamide in citric acid salt form having a particle size range of 0.5 to 150 microns.

In an embodiment, the invention relates to primary particles of N-(5-cyano-4-((2-methoxyethyl)amino)pyridin-2-yl)-7-formyl-6-((4-methyl-2-oxopiperazin-1-yl)methyl)-3,4-dihydro-1,8-naphthyridine-1(2H)-carboxamide in citric acid salt form having a median particle size x50 of between 10 and 20 microns, preferably about 15 microns (see example 3 and FIG. 6). In an embodiment, the x50 value can vary within +/−10%. Thus, in an embodiment, the primary particles of N-(5-cyano-4-((2-methoxyethyl)amino)pyridin-2-yl)-7-formyl-6-((4-methyl-2-oxopiperazin-1-yl)methyl)-3,4-dihydro-1,8-naphthyridine-1(2H)-carboxamide in citric acid salt form have a median particle size x50 of between 9 and 22 microns.

In an embodiment, the invention relates to primary particles of N-(5-cyano-4-((2-methoxyethyl)amino)pyridin-2-yl)-7-formyl-6-((4-methyl-2-oxopiperazin-1-yl)methyl)-3,4-dihydro-1,8-naphthyridine-1(2H)-carboxamide in citric acid salt form having an x10 particle size of between 1 and 5 microns, preferably about 3 microns (see example 3 and FIG. 6). In an embodiment, the x10 value can vary within +/−10%. Thus, in an embodiment, the particles of N-(5-cyano-4-((2-methoxyethyl)amino)pyridin-2-yl)-7-formyl-6-((4-methyl-2-oxopiperazin-1-yl)methyl)-3,4-dihydro-1,8-naphthyridine-1(2H)-carboxamide in citric acid salt form have a x10 value of 0.9 to 5.5 microns. In an embodiment, the invention relates to particles of N-(5-cyano-4-((2-methoxyethyl)amino)pyridin-2-yl)-7-formyl-6-((4-methyl-2-oxopiperazin-1-yl)methyl)-3,4-dihydro-1,8-naphthyridine-1(2H)-carboxamide in citric acid salt form having a particle size x90 of between 50 and 70 microns, preferably about 60 microns (see example 3 and FIG. 6). In an embodiment, the x90 value can vary within +/−10%. Thus, in an embodiment, the particles of N-(5-cyano-4-((2-methoxyethyl)amino)pyridin-2-yl)-7-formyl-6-((4-methyl-2-oxopiperazin-1-yl)methyl)-3,4-dihydro-1,8-naphthyridine-1(2H)-carboxamide in citric acid salt form have a particle size x90 of between 45 and 77 microns.

Figure 2:
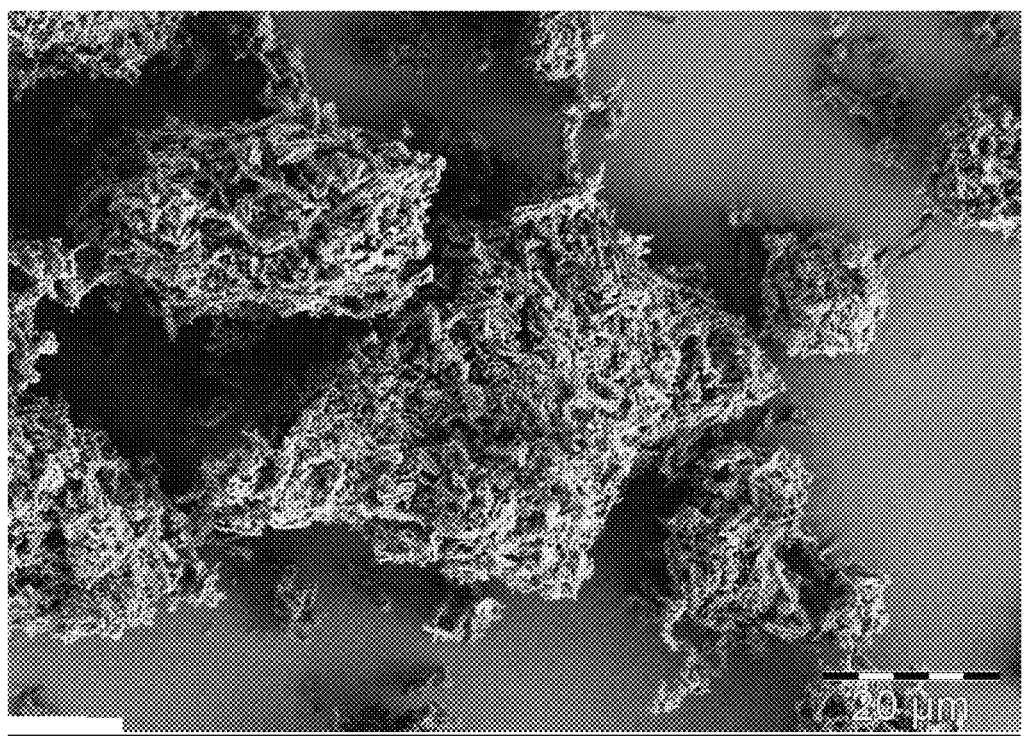
FIG. 2 is a scanning electron micrograph (SEM) of the particles obtained using the process described in PCT/IB2014/065585 (scale 20 microns). The image was taken using a SEM apparatus from Zeiss equipped with a Supra 40 microscope. It shows clumps of needle-shaped primary particles.

The difference in particle sizes between the primary particles of the present invention and those obtained by the process described in PCT/IB2014/065585 can also be seen in the scanning electron microscopy images shown in FIG. 1 and FIG. 2 respectively.

In an embodiment, the primary particles of the present invention have a columnar crystal shape. This can be seen in FIG. 1 and FIG. 8.

In an embodiment, the invention relates to a crystalline primary particle of N-(5-cyano-4-((2-methoxyethyl)amino)pyridin-2-yl)-7-formyl-6-((4-methyl-2-oxopiperazin-1-yl)methyl)-3,4-dihydro-1,8-naphthyridine-1(2H)-carboxamide in citric acid salt form having a columnar crystal shape. A columnar crystal shape is depicted for example in FIG. 1. The crystal shape of the primary particles of the present invention is different from the crystal shape of the particles obtained using the process described in PCT/IB2014/065585 and shown in FIG. 2.

Figure 5:
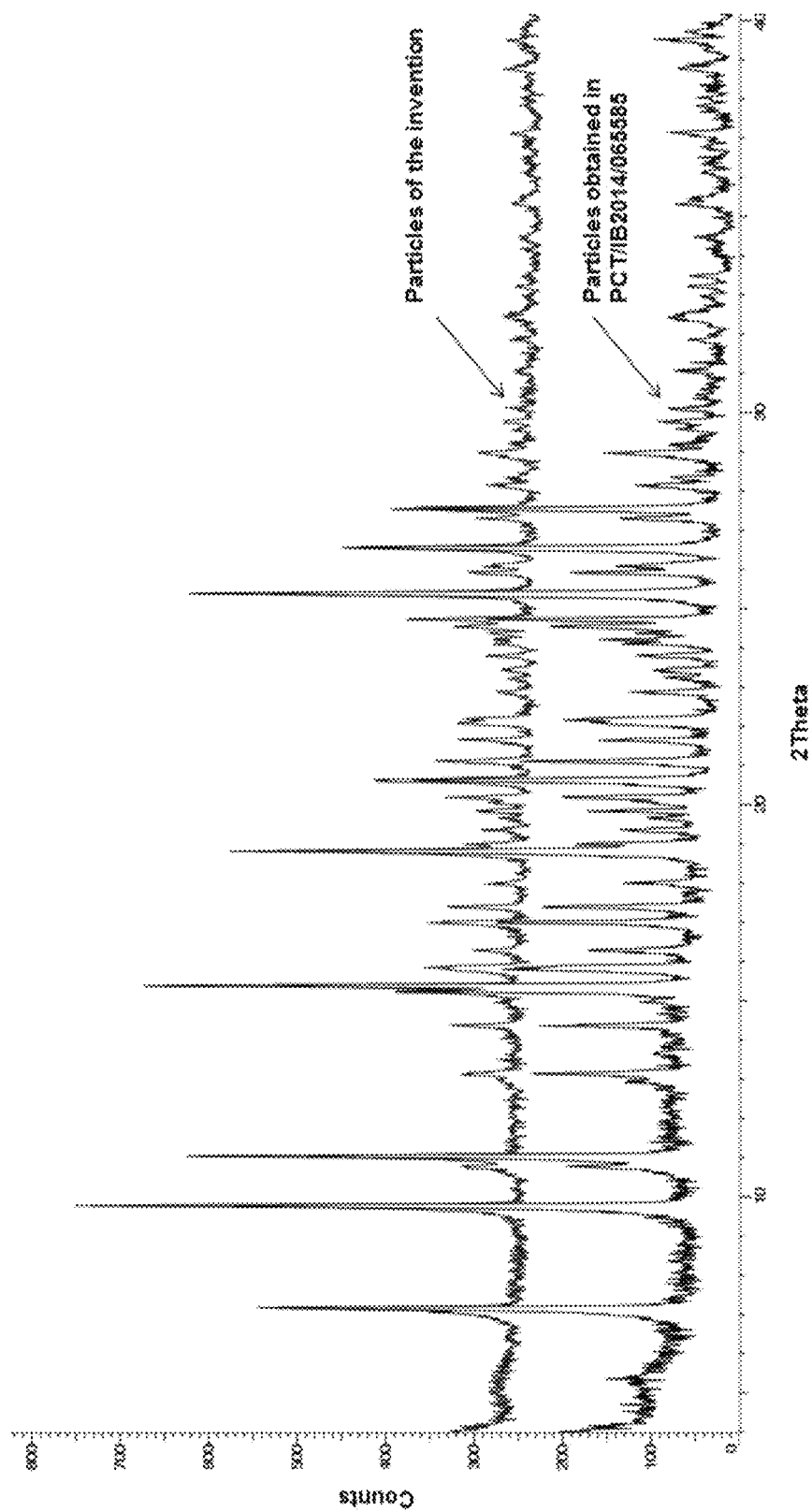
FIG. 5 shows an overlay of the XRPD of the particles obtained using a process of the invention and the XRPD of the particles obtained using the process described in PCT/IB2014/065585. The overlay shows the same signature for both particles of the invention and particles obtained using the process described in PCT/IB2014/065585.

Interestingly, the polymorphic form obtained using the process of the invention or the process described in PCT/IB2014/065585 to generate N-(5-cyano-4-((2-methoxyethyl)amino)pyridin-2-yl)-7-formyl-6-((4-methyl-2-oxopiperazin-1-yl)methyl)-3,4-dihydro-1,8-naphthyridine-1(2H)-carboxamide in citric acid salt form is identical, as can be seen in FIG. 5.

Figure 3:
FIG. 3 is a scanning electron micrograph (SEM) of the particles obtained using a process of the invention (scale 100 microns). The image was taken using a SEM apparatus from Zeiss equipped with a Supra 40 microscope. The figure shows an agglomerate of primary particles. In the agglomerate, the primary particles having a columnar crystal shape are visible.
Figure 4:
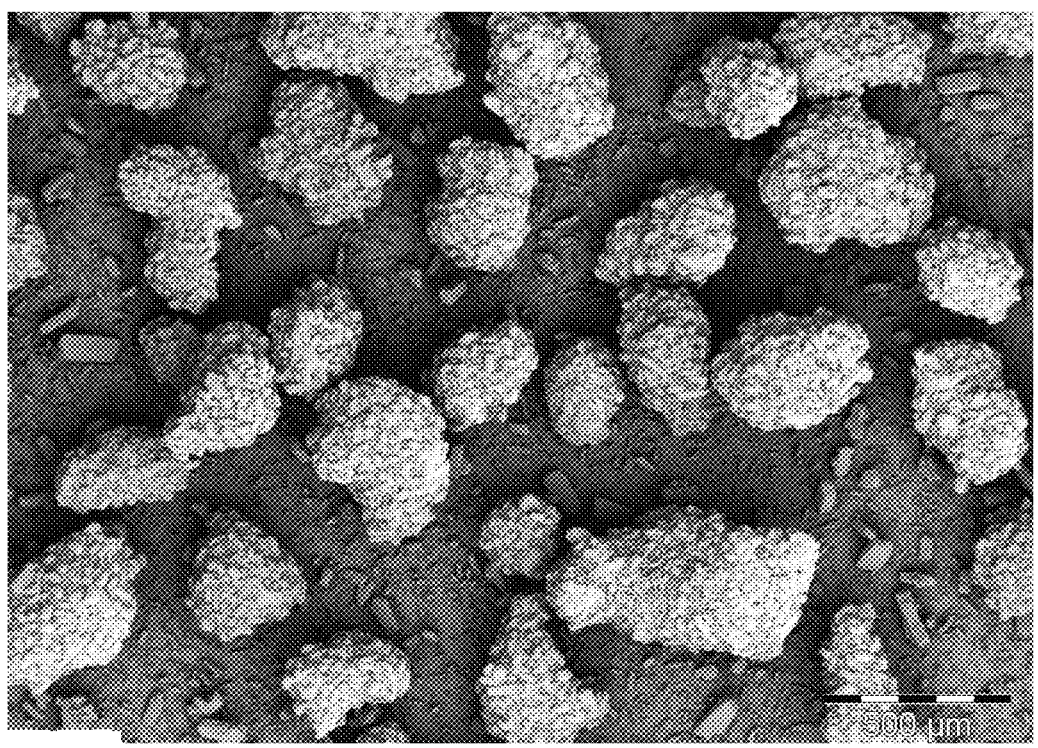
FIG. 4 is a scanning electron micrograph (SEM) of the particles obtained using a process of the invention (scale 500 microns). The image was taken using a SEM apparatus from Zeiss equipped with a Supra 40 microscope. The figure shows agglomerates of primary particles.

The invention also relates, in another aspect, to an agglomerate comprising primary particles of N-(5-cyano-4-((2-methoxyethyl)amino)pyridin-2-yl)-7-formyl-6-((4-methyl-2-oxopiperazin-1-yl)methyl)-3,4-dihydro-1,8-naphthyridine-1(2H)-carboxamide in citric acid salt form as described herein. The agglomerates of the invention can be seen in FIGS. 3 and 4.

Therefore, in an embodiment, the invention relates to an agglomerate comprising primary particles of N-(5-cyano-4-((2-methoxyethyl)amino)pyridin-2-yl)-7-formyl-6-((4-methyl-2-oxopiperazin-1-yl)methyl)-3,4-dihydro-1,8-naphthyridine-1(2H)-carboxamide in citric acid salt form, which agglomerate is obtainable by a process of the invention described herein.

In another embodiment, the invention relates to an agglomerate comprising primary particles of N-(5-cyano-4-((2-methoxyethyl)amino)pyridin-2-yl)-7-formyl-6-((4-methyl-2-oxopiperazin-1-yl)methyl)-3,4-dihydro-1,8-naphthyridine-1(2H)-carboxamide in citric acid salt form, the primary particles having a median particle size ($x50$ or $d50$) of 10 to 20 microns, preferably about 15 microns. In an embodiment, the $x50$ value of the primary particles can vary within +/−10%. Thus, in an embodiment, the invention relates to an agglomerate comprising primary particles of N-(5-cyano-4-((2-methoxyethyl)amino)pyridin-2-yl)-7-formyl-6-((4-methyl-2-oxopiperazin-1-yl)methyl)-3,4-dihydro-1,8-naphthyridine-1(2H)-carboxamide in citric acid salt form having a median particle size $x50$ of between 9 and 22 microns. The agglomerate itself has a median size ($x50$ or $d50$) of between 300 and 400 microns, preferably about 340 microns. In an embodiment, the $x50$ value of the agglomerate can vary within +/−10%. Thus, in an embodiment, the agglomerate comprising primary particles of N-(5-cyano-4-((2-methoxyethyl)amino)pyridin-2-yl)-7-formyl-6-((4-methyl-2-oxopiperazin-1-yl)methyl)-3,4-dihydro-1,8-naphthyridine-1(2H)-carboxamide in citric acid salt form has a median size $x50$ of between 270 and 440 microns.

In another embodiment, the invention relates to an agglomerate comprising primary particles of N-(5-cyano-4-((2-methoxyethyl)amino)pyridin-2-yl)-7-formyl-6-((4-methyl-2-oxopiperazin-1-yl)methyl)-3,4-dihydro-1,8-naphthyridine-1(2H)-carboxamide in citric acid salt form, the primary particles having a particle size ($x10$ or $d10$) of between 1 and 5 microns, preferably about 3 microns. In an embodiment, the $x10$ value of the primary particles can vary within +/−10%. Thus, in an embodiment, the invention relates to an agglomerate comprising primary particles of N-(5-cyano-4-((2-methoxyethyl)amino)pyridin-2-yl)-7-formyl-6-((4-methyl-2-oxopiperazin-1-yl)methyl)-3,4-dihydro-1,8-naphthyridine-1(2H)-carboxamide in citric acid salt form having a $x10$ value of 0.9 to 5.5 microns. The agglomerate itself has a size $x10$ or $d10$ of between 200 and 300 microns, preferably about 230 microns. In an embodiment, the $x10$ value of the agglomerate can vary within +/−10%. Thus, in an embodiment, the agglomerate comprising primary particles of N-(5-cyano-4-((2-methoxyethyl)amino)pyridin-2-yl)-7-formyl-6-((4-methyl-2-oxopiperazin-1-yl)methyl)-3,4-dihydro-1,8-naphthyridine-1(2H)-carboxamide in citric acid salt form has a size $x10$ of between 180 and 330 microns.

In another embodiment, the invention relates to an agglomerate comprising primary particles of N-(5-cyano-4-((2-methoxyethyl)amino)pyridin-2-yl)-7-formyl-6-((4-methyl-2-oxopiperazin-1-yl)methyl)-3,4-dihydro-1,8-naphthyridine-1(2H)-carboxamide in citric acid salt form having a particle size $x90$ or $d90$ of between 50 and 70 microns, preferably about 60 microns. In an embodiment, the $x90$ value of the primary particles can vary within +/−10%. Thus, in an embodiment, the invention relates to an agglomerate comprising primary particles of N-(5-cyano-4-((2-methoxyethyl)amino)pyridin-2-yl)-7-formyl-6-((4-methyl-2-oxopiperazin-1-yl)methyl)-3,4-dihydro-1,8-naphthyridine-1(2H)-carboxamide in citric acid salt form having a particle size $x90$ of between 45 and 77 microns.

The agglomerate itself has a size $x90$ or $d90$ of between 450 and 550 microns, preferably about 490 microns. In an embodiment, the $x90$ value of the agglomerate can vary within +/−10%. Thus, in an embodiment, the agglomerate comprising primary particles of N-(5-cyano-4-((2-methoxyethyl)amino)pyridin-2-yl)-7-formyl-6-((4-methyl-2-oxopiperazin-1-yl)methyl)-3,4-dihydro-1,8-naphthyridine-1(2H)-carboxamide in citric acid salt form has a size $x90$ of between 405 and 605 microns.

Without wishing to be bound by theory, it is thought that the agglomerates are formed upon drying of the primary particles obtained in step b) of the process of the invention. The formation of agglomerate may be due to residual solvent on the surface of the primary particles which may induce the formation of agglomerate.

The particles described herein may be used in the manufacture of a pharmaceutical composition. Therefore, the invention relates, in one embodiment, to a pharmaceutical composition comprising particles of N-(5-cyano-4-((2-methoxyethyl)amino)pyridin-2-yl)-7-formyl-6-((4-methyl-2-oxopiperazin-1-yl)methyl)-3,4-dihydro-1,8-naphthyridine-1(2H)-carboxamide in citric acid salt form as described herein and optionally one or more pharmaceutically acceptable carrier(s).

In an embodiment, the pharmaceutical composition comprises particles of N-(5-cyano-4-((2-methoxyethyl)amino)pyridin-2-yl)-7-formyl-6-((4-methyl-2-oxopiperazin-1-yl)methyl)-3,4-dihydro-1,8-naphthyridine-1(2H)-carboxamide in citric acid salt form and no pharmaceutically acceptable carrier(s). In an embodiment, the pharmaceutical composition comprises a therapeutically effective amount of particles of N-(5-cyano-4-((2-methoxyethyl)amino)pyridin-2-yl)-7-formyl-6-((4-methyl-2-oxopiperazin-1-yl)methyl)-3,4-dihydro-1,8-naphthyridine-1(2H)-carboxamide in citric acid salt form and one or more pharmaceutically acceptable carriers.

In another aspect, the present invention provides a pharmaceutical composition comprising particles of N-(5-cyano-4-((2-methoxyethyl)amino)pyridin-2-yl)-7-formyl-6-((4-methyl-2-oxopiperazin-1-yl)methyl)-3,4-dihydro-1,8-naphthyridine-1(2H)-carboxamide in citric acid salt form and a pharmaceutically acceptable carrier. In a further embodiment, the composition comprises at least two pharmaceutically acceptable carriers, such as those described herein. For purposes of the present invention, unless designated otherwise, solvates and hydrates are generally considered compositions. Preferably, pharmaceutically acceptable carriers are sterile. The pharmaceutical composition can be formulated for particular routes of administration such as oral administration, parenteral administration, and rectal administration, etc. In addition, the pharmaceutical compositions of the present invention can be made up in a solid form (including without limitation capsules, tablets, pills, granules, powders or suppositories), or in a liquid form (including without limitation solutions, suspensions or emulsions). The pharmaceutical compositions can be subjected to conventional pharmaceutical operations such as sterilization and/or can contain conventional inert diluents, lubricating agents, or buffering agents, as well as adjuvants, such as preservatives, stabilizers, wetting agents, emulsifiers and buffers, etc.

Typically, the pharmaceutical compositions are tablets or gelatin capsules comprising the active ingredient together with one or more of:

a) diluents, e.g., lactose, dextrose, sucrose, mannitol, sorbitol, cellulose and/or glycine;
b) lubricants, e.g., silica, talcum, stearic acid, its magnesium or calcium salt and/or polyethyleneglycol;
c) binders, e.g., magnesium aluminum silicate, starch paste, gelatin, tragacanth, methylcellulose, sodium carboxymethylcellulose and/or polyvinylpyrrolidone;
d) disintegrants, e.g., starches, agar, alginic acid or its sodium salt, or effervescent mixtures; and
e) absorbents, colorants, flavors and sweeteners.

In an embodiment, the pharmaceutical composition is in the form of a capsule comprising the active ingredient only. In another embodiment, the pharmaceutical composition is in the form of a capsule comprising a blend of the active ingredient and excipients. Tablets may be either film coated or enteric coated according to methods known in the art.

Suitable compositions for oral administration include an effective amount of a compound of the invention in the form of tablets, lozenges, aqueous or oily suspensions, dispersible powders or granules, emulsion, hard or soft capsules, or syrups or elixirs, solutions or solid dispersion. Compositions intended for oral use are prepared according to any method known in the art for the manufacture of pharmaceutical compositions and such compositions can contain one or more agents selected from the group consisting of sweetening agents, flavoring agents, coloring agents and preserving agents in order to provide pharmaceutically elegant and palatable preparations. Tablets may contain the active ingredient in admixture with nontoxic pharmaceutically acceptable excipients which are suitable for the manufacture of tablets. These excipients are, for example, inert diluents, such as calcium carbonate, sodium carbonate, lactose, calcium phosphate or sodium phosphate; granulating and disintegrating agents, for example, corn starch, or alginic acid; binding agents, for example, starch, gelatin or acacia; and lubricating agents, for example magnesium stearate, stearic acid or talc. The tablets are uncoated or coated by known techniques to delay disintegration and absorption in the gastrointestinal tract and thereby provide a sustained action over a longer period. For example, a time delay material such as glyceryl monostearate or glyceryl distearate can be employed. Formulations for oral use can be presented as hard gelatin capsules wherein the active ingredient is mixed with an inert solid diluent, for example, calcium carbonate, calcium phosphate or kaolin, or as soft gelatin capsules wherein the active ingredient is mixed with water or an oil medium, for example, peanut oil, liquid paraffin or olive oil.

Figure 9:
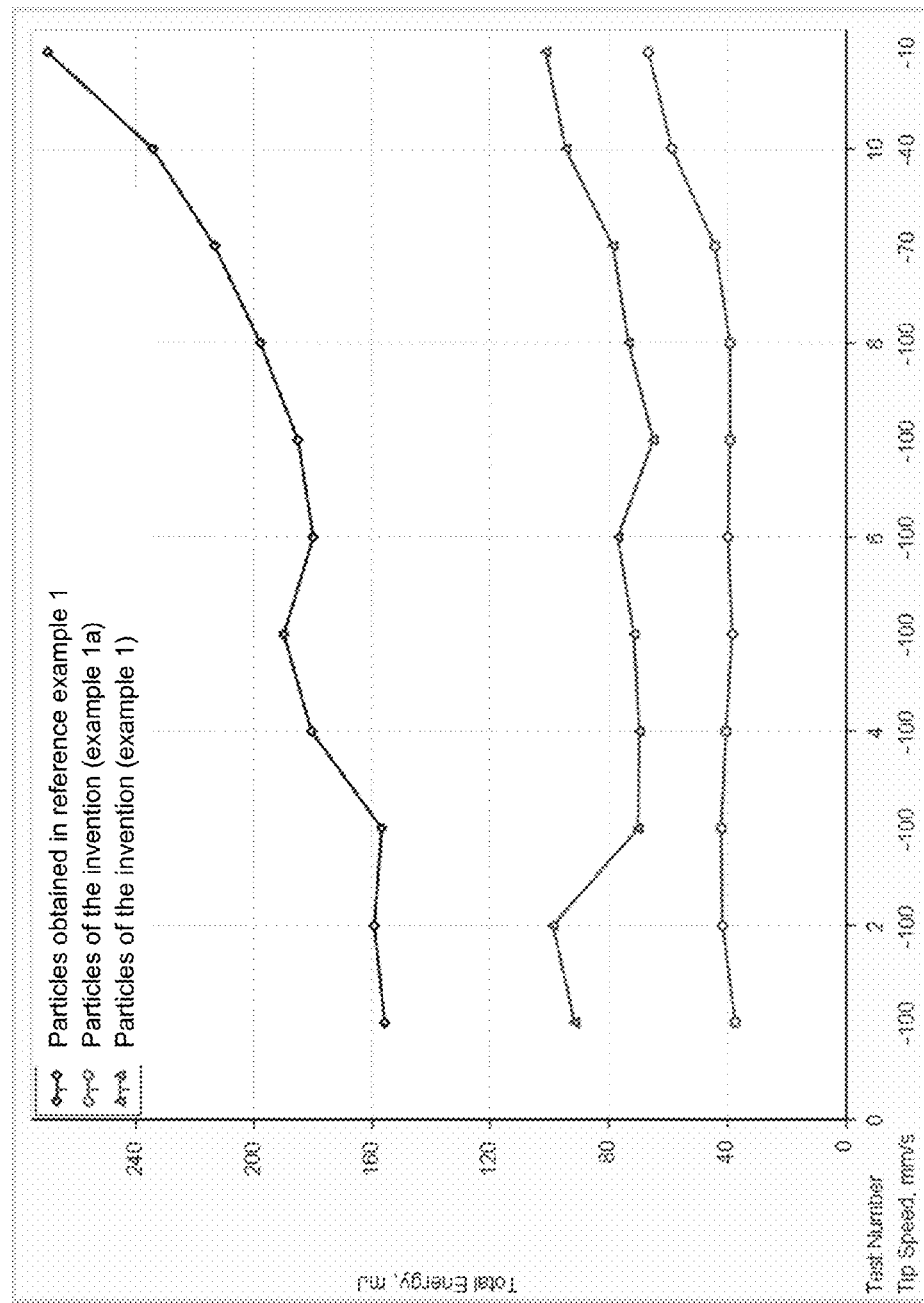
FIG. 9 shows the basic flow energy of the particles of the invention as described in examples 1 and 1a and of particles obtained using the process described in PCT/IB2014/065585 (reference example 1). The graph shows that the particles of the invention require less energy to flow compared to those obtained by the process described in PCT/IB2014/065585 (reference example 1), indicating improved flowability.
Figure 10:
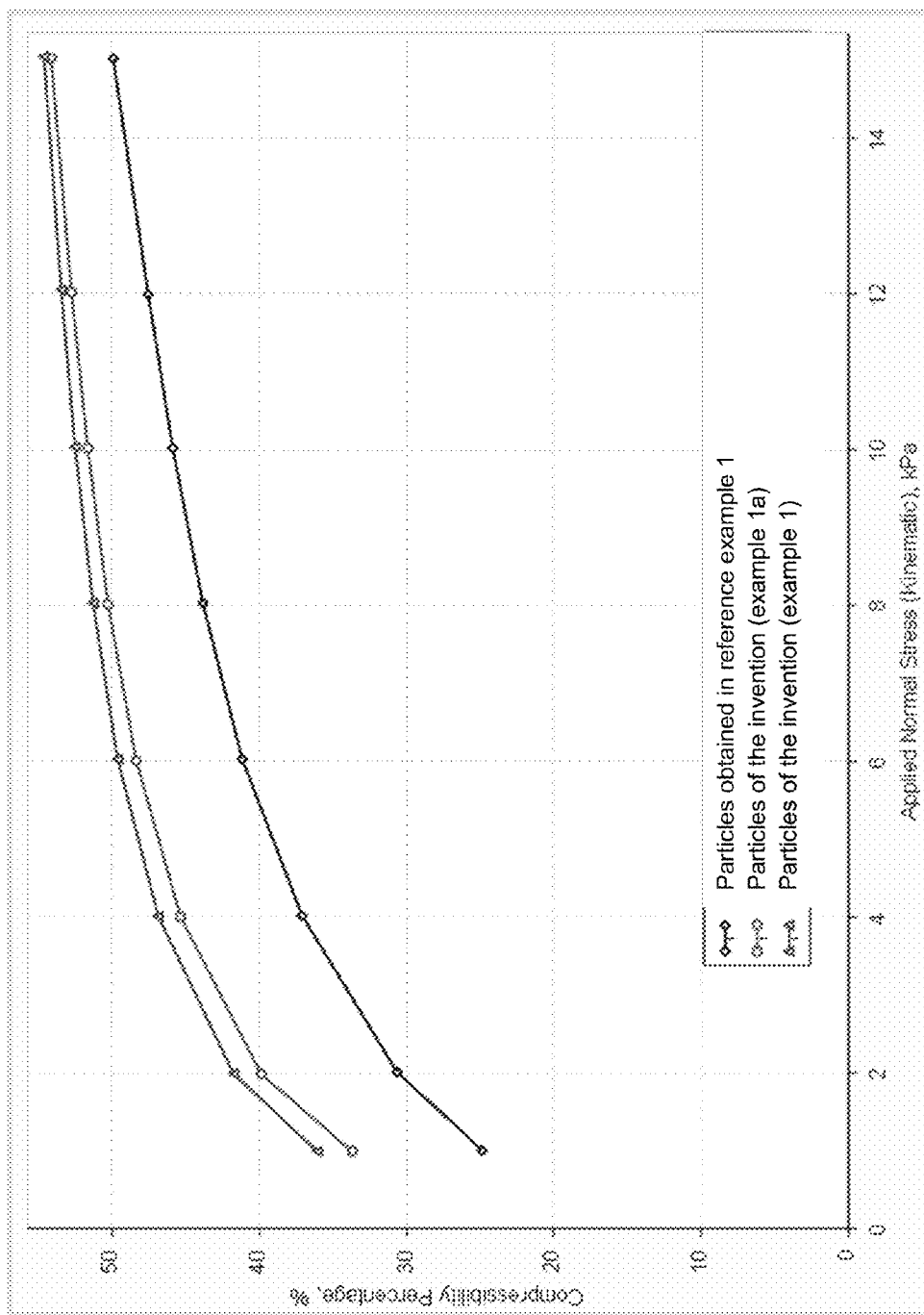
FIG. 10 shows the compressibility percentage as a function of applied normal stress of the particles of the invention as described in examples 1 and 1a and of particles obtained using the process described in PCT/IB2014/065585 (reference example 1). The graph shows that the particles of the invention have a higher compressibility percentage, suggesting that higher drug load in the final drug product could be achieved by using the particles of the invention.

The particles of the invention offer beneficial properties in terms of ease of processability. Indeed, the flow properties of the particles of the invention are improved compared to the flow properties of the particles obtained using the process described in PCT/IB2014/065585 (reference example 1). Flow properties can be quantified by powder rheometry. Powder rheometry allows to measure a number of parameters on drug substances such as basic flow energy, compressibility percentage, wall friction angle. As can be seen in FIG. 9, the particles of the invention differ at least significantly in the basic flow energy compared to those obtained using the process described in PCT/IB2014/065585. This suggests that the particles of the invention offer advantages in terms of processability. Also, as can be seen in FIG. 10, the compressibility percentage is increased with the particles of the present invention compared to those obtained by the process described in PCT/IB2014/065585. This suggests that drug load could be improved in the drug product manufacture.

Figure 11:
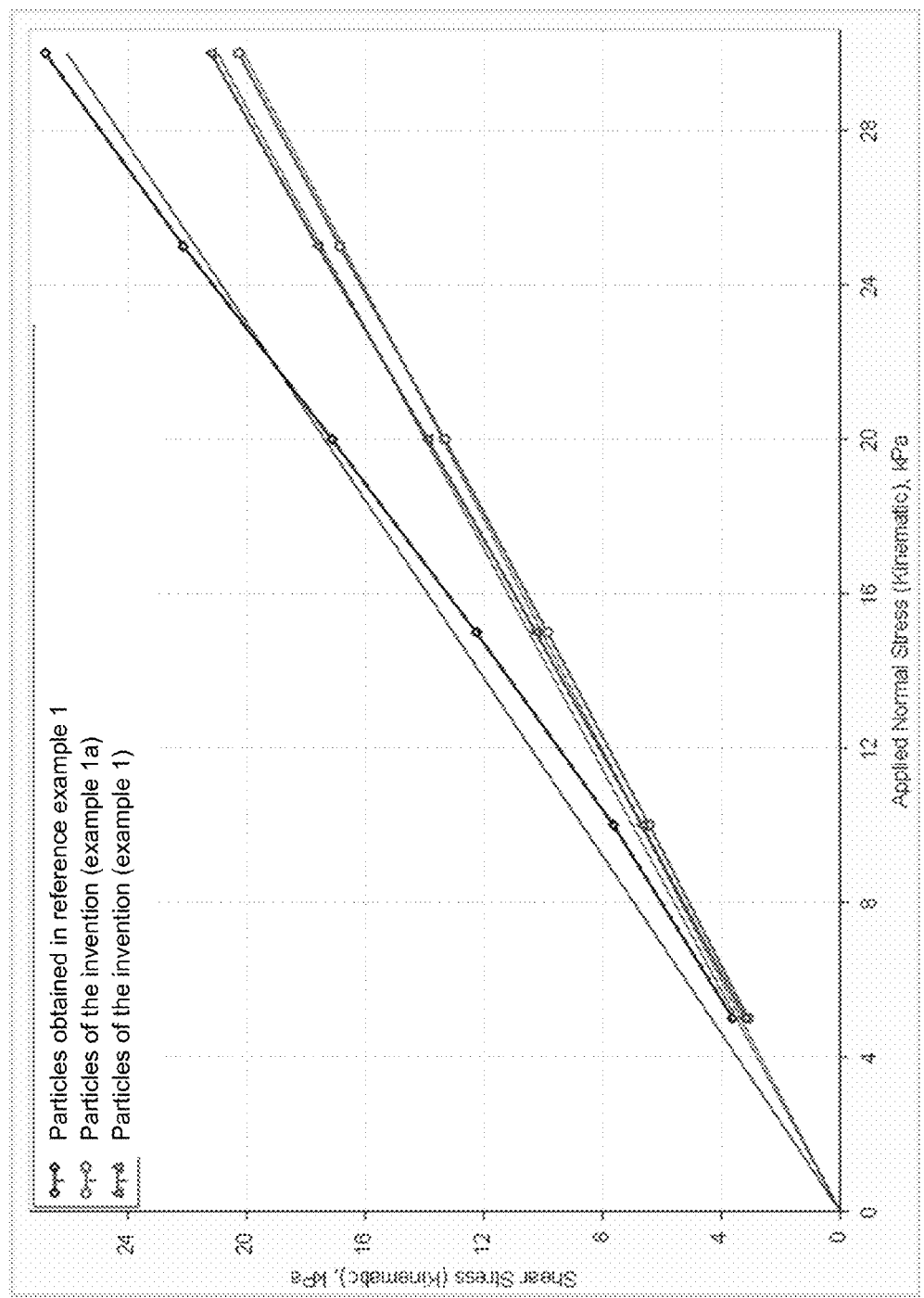
FIG. 11 shows the plots of the shear stress as a function of the applied normal stress of the particles of the invention as described in examples 1 and 1a and of particles obtained using the process described in PCT/IB2014/065585 (reference example 1). This enables to calculate a wall friction angle. The graph shows that the particles of the invention have a lower wall friction angle compared to those obtained using the process described in PCT/IB2014/065585 (reference example 1) indicating that the particles of the invention exhibit less sticky behaviour to metal surfaces and thus improved processability.

In addition, as can be seen in FIG. 11, the wall friction angle differs between the particles of the present invention and those obtained by the process described in PCT/IB2014/065585. This indicates that the surface characteristics of the particles are different and suggests that the present particles exhibit a less sticky behaviour (less interaction with stainless steel). This again provides advantages in terms of processability when using the particles of the present invention.

The use of the present particles facilitates the drug product manufacture, for instance capsule filling, giving higher yields (compared to using the particles obtained by the process described in PCT/IB2014/065585). In addition, using the present particles, it may be possible to reduce the amount of excipients needed for the drug product manufacture which offers advantages in terms of cost, time and process efficiency. Indeed, if a drug substance is sticky or does not flow easily, more excipients may be needed to improve the handling of said drug substance.

The pharmaceutical composition of the present invention can be in unit dosages of about 1-1000 mg of active ingredient for a subject of about 50-70 kg, or about 1-500 mg or about 1-250 mg or about 1-150 mg or about 0.5-100 mg, or about 1-50 mg of active ingredient. In one embodiment, it is about 50 mg of active ingredient. In another embodiment, it is about 100 mg of active ingredient. In another embodiment, it is about 200 mg of active ingredient. In another embodiment, it is about 300 mg of active ingredient. The therapeutically effective dosage of the pharmaceutical composition is dependent on the species of the subject, the body weight, age and individual condition, the disorder or disease or the severity thereof being treated. A physician, clinician or veterinarian of ordinary skill can readily determine the effective amount of the active ingredient necessary to prevent, treat or inhibit the progress of the disorder or disease.

The activity of N-(5-cyano-4-((2-methoxyethyl)amino)pyridin-2-yl)-7-formyl-6-((4-methyl-2-oxopiperazin-1-yl)methyl)-3,4-dihydro-1,8-naphthyridine-1(2H)-carboxamide is shown in example 2.

Having regard to the activity of N-(5-cyano-4-((2-methoxyethyl)amino)pyridin-2-yl)-7-formyl-6-((4-methyl-2-oxopiperazin-1-yl)methyl)-3,4-dihydro-1,8-naphthyridine-1(2H)-carboxamide as an FGFR4 inhibitor, the pharmaceutical composition of the invention may be useful in the treatment of conditions which are mediated by the activity of FGFR4 proteins, such as cancer, and/or that are responsive (meaning especially in a therapeutically beneficial way) to inhibition of FGFR4, most especially a disease or disorder as mentioned herein below.

The pharmaceutical composition of the invention may be useful in the treatment of cancer. In particular, the pharmaceutical composition of the invention may be useful in the treatment of an indication selected from liver cancer, breast cancer, glioblastoma, prostate cancer, rhabdomyosarcoma, gastric cancer, ovarian cancer, lung cancer, colon cancer.

Thus, as a further embodiment, the present invention provides the use of a pharmaceutical composition comprising particles of N-(5-cyano-4-((2-methoxyethyl)amino)pyridin-2-yl)-7-formyl-6-((4-methyl-2-oxopiperazin-1-yl)methyl)-3,4-dihydro-1,8-naphthyridine-1(2H)-carboxamide in citric acid salt form as described herein, in therapy. In a further embodiment, the therapy is selected from a disease which may be treated by inhibition of FGFR4. In another embodiment, the disease is selected from the afore-mentioned list, suitably liver cancer.

Thus, as a further embodiment, the present invention provides a pharmaceutical composition comprising particles of N-(5-cyano-4-((2-methoxyethyl)amino)pyridin-2-yl)-7-formyl-6-((4-methyl-2-oxopiperazin-1-yl)methyl)-3,4-dihydro-1,8-naphthyridine-1(2H)-carboxamide in citric acid salt form as described herein for use in therapy. In a further embodiment, the therapy is for a disease which may be treated by inhibition of FGFR4. In another embodiment, the disease is selected from the afore-mentioned list, suitably liver cancer.

In another embodiment, the invention provides a method of treating a disease which is treated by inhibition of FGFR4 comprising administration of a therapeutically effective amount of a pharmaceutical composition comprising particles of N-(5-cyano-4-((2-methoxyethyl)amino)pyridin-2-yl)-7-formyl-6-((4-methyl-2-oxopiperazin-1-yl)methyl)-3,4-dihydro-1,8-naphthyridine-1(2H)-carboxamide in citric acid salt form as described herein. In a further embodiment, the disease is selected from the afore-mentioned list, suitably liver cancer.

Thus, as a further embodiment, the present invention provides the use of particles of N-(5-cyano-4-((2-methoxyethyl)amino)pyridin-2-yl)-7-formyl-6-((4-methyl-2-oxopiperazin-1-yl)methyl)-3,4-dihydro-1,8-naphthyridine-1(2H)-carboxamide in citric acid salt form as described herein, for the manufacture of a medicament. In a further embodiment, the medicament is for treatment of a disease which may be treated by inhibition of FGFR4. In another embodiment, the disease is selected from the afore-mentioned list, suitably liver cancer.

The pharmaceutical composition of the invention may also be useful in the treatment of solid malignancies characterized by positive FGFR4 expression.

The pharmaceutical composition of the invention may also be useful in the treatment of solid malignancies characterized by positive KLB (beta-klotho) expression.

The pharmaceutical composition of the invention may also be useful in the treatment of solid malignancies characterized by positive FGF19 expression.

The pharmaceutical composition of the invention may also be useful in the treatment of solid malignancies characterized by positive FGFR4 and positive KLB expression.

The pharmaceutical composition of the invention may also be useful in the treatment of solid malignancies characterized by positive FGFR4 and positive FGF19 expression.

The pharmaceutical composition of the invention may also be useful in the treatment of solid malignancies characterized by positive FGFR4, positive KLB and positive FGF19 expression.

Any positive expression in FGFR4, KLB and/or FGF19 as described above can be assessed by methods known to the skilled person such as e.g. RT-qPCR, Western blotting, ELISA, immunohistochemistry.

EXAMPLES

The following examples are intended to illustrate the invention and are not to be construed as being limitations thereon. Temperatures are given in degrees Celsius. If not mentioned otherwise, all evaporations are performed under reduced pressure, typically between about 15 mm Hg and 100 mm Hg (=20-133 mbar). The structure of final products, intermediates and starting materials is confirmed by standard analytical methods, e.g., microanalysis and spectroscopic characteristics, e.g., MS, IR, NMR. Abbreviations used are those conventional in the art.

All starting materials, building blocks, reagents, acids, bases, dehydrating agents, solvents, and catalysts utilized to synthesise the compounds of the present invention are either commercially available or can be produced by organic synthesis methods known to one of ordinary skill in the art. Further, the compounds of the present invention can be produced by organic synthesis methods known to one of ordinary skill in the art as shown in the following examples.

Abbreviations

| Abbreviation | Description |
|---|---|
| aq. | aqueous |
| conc. | concentrated |
| DAST | (diethylamino)sulfur trifluoride |
| dba | dibenzylideneacetone |
| DCC | Dicyclohexylcarbodiimide |
| DCM | dichloromethane |
| DIPEA | N,N-diisopropylethylamine, N-ethyl-N-isopropylpropan-2-amine |
| DMA | N,N-dimethylacetamide |
| DMAP | 4-dimethylaminopyridine |
| DME | 1,2-dimethoxyethane |
| DMF | N,N-dimethylformamide |
| DMSO | dimethylsulfoxide |
| DMSO-$d_6$ | Hexadeuterodimethyl sulfoxide |
| dppf | 1,1'-bis(diphenylphosphino)ferrocene |
| DSC | Differential scanning calorimetry |
| ESI-MS | Electrospray ionization mass spectroscopy |
| h | hour |
| HPLC | High-performance liquid chromatography |
| KHMDS | Potassium hexamethyldisilazide |
| L/mL | litre/millilitre |
| LC-MS | liquid chromatography and mass spectrometry |
| LHMDS | Lithium hexamethyldisilazide |
| M | molar |
| min | minutes |
| mp | Melting point |
| MW | microwave |
| mw | Molecular weight |
| m/z | mass to charge ratio |
| NBS | N-bromosuccinimide |
| NCS | N-chlorosuccinimide |
| NIS | N-iodosuccinimide |
| NMP | N-methylpyrrolidinone, 1-methyl-2-pyrrolidinone |
| NMR | Nuclear magnetic resonance |
| org. | organic |
| RP | Reverse phase |
| sat | saturated |
| SFC | Supercritical fluid chromatography |
| TBAF | tetrabutylammonium fluoride |
| TFA | trifluoroacetic acid |
| THF | tetrahydrofurane |
| $t_R$ or Rt | Retention time (if not indicated, in minutes) |
| UPLC | Ultra-performance liquid chromatography |

Analytical Details
NMR:
Measurements were performed on a Bruker Ultrashield™ 400 (400 MHz), Bruker Ultrashield™ 600 (600 MHz), 400 MHz DRX Bruker CryoProbe (400 MHz) or a 500 MHz DRX Bruker CryoProbe (500 MHz) spectrometer using or not trimethylsilane as an internal standard. Chemical shifts (d-values) are reported in ppm downfield from tetramethylsilane, spectra splitting pattern are designated as singlet (s), doublet (d), triplet (t), quartet (q), multiplet, unresolved or more overlapping signals (m), broad signal (br). Solvents are given in parentheses.
DSC:
DSC measurements were performed using a DSC Q2000 (TA Instruments, New Castle, Del., USA) equipped with a DSC Refrigerated Cooling System (TA Instruments, New Castle, Del., USA). Data were treated mathematically using the resident Universal Analysis® Software. Calibration for temperature and heat of fusion was carried out with indium as reference material. The samples were analyzed in open aluminium pans and scanned under a nitrogen purge with a heating rate of 10° C./min from 20 to 300° C.
UPLC-MS 3:
System: Waters Acquity UPLC with Waters SQ detector.
Column: Acquity HSS T3 1.8 μm 2.1×50 mm.
Flow: 1.0 mL/min. Column temperature: 60° C.
Gradient: from 5 to 98% B in 1.4 min, A=water+0.05% formic acid+3.75 mM ammonium acetate, B=acetonitrile+ 0.04% formic acid.
UPLC-MS 6:
System: Waters Acquity Ultra Performance with Waters SQ detector.
Column: Acquity HSS T3 1.8 μm 2.1×50 mm.
Flow: 1.0 mL/min. Column temperature: 60° C.
Gradient: from 5 to 98% B in 1.4 min, A=water+0.05% formic acid+3.75 mM ammonium acetate, B=acetonitrile+ 0.04% formic acid.
ESI-MS:
Water Acquity™ Ultra performance LC Example 1—N-(5-cyano-4-((2-methoxyethyl)amino) pyridin-2-yl)-7-formyl-6-((4-methyl-2-oxopiperazin-1-yl)methyl)-3,4-dihydro-1,8-naphthyridine-1(2H)-carboxamide in citric acid salt form 1:1

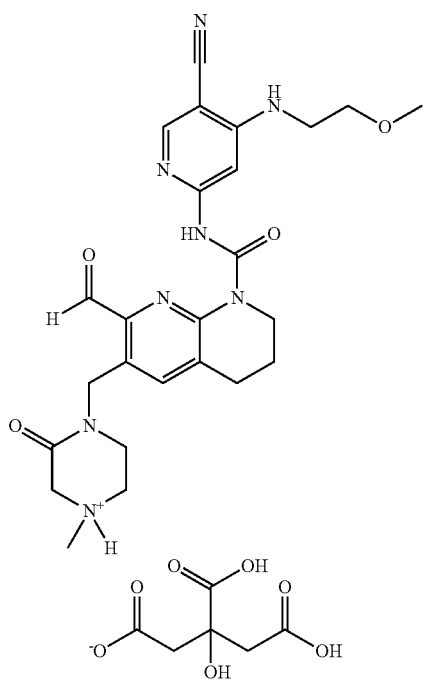

Step 1: 2-(dimethoxymethyl)-1,8-naphthyridine

The procedure described in *J. Org. Chem.*, 2004, 69 (6), pp 1959-1966 was used. Into a 20 L 4-necked round-bottom flask was placed 2-aminopyridine-3-carbaldehyde (1000 g, 8.19 mol), 1,1-dimethoxypropan-2-one (1257 g, 10.64 mol), ethanol (10 L), and water (2 L). This was followed by the addition of a solution of sodium hydroxide (409.8 g, 10.24 mol) in water (1000 mL) drop wise with stirring at 0-15° C.

The solution was stirred for 3 h at 0-20° C. and then concentrated under vacuum. The resulting solution was extracted with 3×1200 mL of ethyl acetate and the organic layers were combined. The mixture was dried over sodium sulfate and concentrated under vacuum. The residue was washed with 3×300 mL of hexane and the solid was collected by filtration. This resulted in the title compound as a yellow solid. $^1$H-NMR (400 MHz, DMSO-d$_6$) δ 9.11 (dd, 1H), 8.53 (d, 1H), 8.50 (dd, 1H), 7.73 (d, 1H), 7.67 (dd, 1H), 5.44 (s, 1H), 3.41 (s, 6H).

Step 2: 7-(dimethoxymethyl)-1,2,3,4-tetrahydro-1,8-naphthyridine

The procedure described in *J. Org. Chem.*, 2004, 69 (6), pp 1959-1966 was used. Into a 5-L pressure tank reactor (5 atm) was placed 2-(dimethoxymethyl)-1,8-naphthyridine (200 g, 979 mmol), ethanol (3 L), PtO$_2$ (12 g). The reactor was evacuated and flushed three times with nitrogen, followed by flushing with hydrogen. The mixture was stirred overnight at 23° C. under an atmosphere of hydrogen. This reaction was repeated four times. The solids were filtered out and the resulting mixture was concentrated under vacuum to give the title compound as a yellow solid. $^1$H-NMR (400 MHz, DMSO-d$_6$) δ 7.14 (d, 1H), 6.51 (d, 1H), 6.47-6.41 (m, 1H), 4.98 (s, 1H), 3.28-3.19 (m, 2H), 3.23 (s, 6H), 2.64 (t, 2H), 1.73-1.79 (m, 2H).

Step 3: 6-bromo-7-(dimethoxymethyl)-1,2,3,4-tetrahydro-1,8-naphthyridine

Into a 3 L 4-necked round-bottom flask was placed 7-(dimethoxymethyl)-1,2,3,4-tetrahydro-1,8-naphthyridine (114.6 g, 550.3 mmol) in acetonitrile (2 L). This was followed by the addition of NBS (103 g, 578 mol) in portions with stirring at 25° C. The resulting solution was stirred for 30 min at 25° C. The resulting mixture was concentrated under vacuum and the residue was diluted with 1000 mL of diethylether. The mixture was washed with 3×100 mL of ice/water. The aqueous phase was extracted with 2×100 mL of diethylether and the organic layers were combined. The resulting mixture was washed with 1×100 mL of brine, dried over sodium sulfate and concentrated under vacuum to give the title compound as a light yellow solid. LC-MS: (ES, m/z): 286.03 [M+H]$^+$. $^1$H-NMR: (300 MHz, CDCl$_3$) δ 1.86-1.94 (2H, m), 2.70-2.74 (2H, m), 3.9-3.43 (2H, m), 3.47 (6H, s), 5.23 (1H, s), 5.58 (1H, s), 7.29 (1H, s).

Step 4: 2-(dimethoxymethyl)-5,6,7,8-tetrahydro-1,8-naphthyridine-3-carbaldehyde

To a solution of 6-bromo-7-(dimethoxymethyl)-1,2,3,4-tetrahydro-1,8-naphthyridine (15.0 g, 52.2 mmol) in THF (400 mL) at −78° C. under argon, was added MeLi (1.6 M in Et$_2$O, 32.6 mL, 52.2 mmol), the solution was stirred for 5 min, then n-BuLi (1.6 M in hexane, 35.9 mL, 57.5 mmol) was added slowly and the solution was stirred for 20 min. THF (100 mL) was added to the reaction at −78° C. Subsequently, n-BuLi (1.6 M in hexane, 49.0 mL, 78 mmol) was added and the reaction mixture was stirred for 20 min, then again n-BuLi (1.6 M in hexane, 6.53 mL, 10.45 mmol) was added and the mixture was stirred for 10 min at −78° C. DMF (2.10 mL, 27.2 mmol) was added and the reaction mixture was stirred at −78° C. for 45 min, then it was allowed to warm to room temperature, poured into sat. aq.

NH₄Cl and extracted twice with DCM. The combined organic phases were dried over Na₂SO₄, filtered and evaporated to give the title compound as an orange oil. (UPLC-MS 3) $t_R$ 0.63 min; ESI-MS 237.2 [M+H]⁺.

Step 5: ethyl 2-((2-((tert-butoxycarbonyl)amino) ethyl)(methyl)amino)acetate

Ethyl bromoacetate (1.27 mL, 11.48 mmol) was added to a mixture of tert-butyl (2-(methylamino)ethyl)carbamate (2.0 g, 11.48 mmol), triethylamine (4.81 mL) and THF (24 mL) at 0° C. After stirring 24 h at room temperature the reaction mixture was partitioned between saturated aqueous NaHCO₃ and DCM, extracted 2× with DCM, the organic layers dried over Na₂SO₄ and evaporated to give the title compound as a clear pale-yellow oil. ¹H NMR (400 MHz, CDCl₃) δ 5.20 (s, br, 1H), 4.18 (q, 2H), 3.24 (s, 2H), 3.22-3.16 (m, 2H), 2.65-2.61 (m, 2H), 2.38 (s, 3H), 1.42 (s, 9H), 1.24 (t, 3H).

Step 6: ethyl 2-((2-aminoethyl)(methyl)amino)acetate dihydrochloride

Concentrated hydrochloric acid (10 mL) was added to a solution of ethyl 2-((2-((tert-butoxycarbonyl)amino)ethyl) (methyl)amino)acetate (3.05 g, 11.13 mmol) in THF (20 mL) and EtOH (100 mL) at room temperature. After stirring 1 h at room temperature the reaction mixture was evaporated, ethanol (20 mL) added, evaporated, further ethanol (50 mL) added and then stirred at 60° C. for 70 min. The cooled reaction mixture was then evaporated to give the title compound as a pale-yellow glass. ¹H NMR (400 MHz, DMSO-d₆) δ 8.58 (s, br, 3H), 4.19 (q, 2H), 4.26-4.15 (m, 2H), 3.44 (s, br, 2H), 3.21 (s, br, 2H), 2.88 (s, 3H), 1.21 (t, 3H).

Step 7: 1-((2-(dimethoxymethyl)-5,6,7,8-tetrahydro-1,8-naphthyridin-3-yl)methyl)-4-methylpiperazin-2-one Sodium triacetoxyborohydride (3.10 g, 14.61 mmol) was added to a mixture of 2-(dimethoxymethyl)-5,6,7,8-tetrahydro-1,8-naphthyridine-3-carbaldehyde (obtained in step 4, 2.30 g, 9.74 mmol), ethyl 2-((2-aminoethyl)(methyl) amino)acetate dihydrochloride (obtained in step 6, 2.6 g, 14.61 mmol) and triethylamine (6.75 mL, 48.7 mmol) in 1,2-dichloroethane (20 mL) at room temperature. The reaction mixture was stirred for 21 h at room temperature and additional sodium triacetoxyborohydride (2.6 g, 9.74 mmol) was added. After a further 4 h stirring at room temperature, again additional sodium triacetoxyborohydride (1.3 g, 4.87 mmol) was added and the reaction maintained at 4° C. for 2.5 days. The reaction mixture was then warmed to room temperature, saturated aqueous NaHCO₃ solution added, the mixture extracted with DCM (3×), the combined organic layers dried over Na₂SO₄ and evaporated. The residue was applied to a 120 g RediSep® silica column as a DCM solution and purified by normal phase chromatography, eluting with a gradient from DCM to 10% MeOH in DCM. Product containing fractions were combined and evaporated to give the title compound as an orange foam. ¹H NMR (400 MHz, CDCl₃) δ 7.08 (s, 1H), 5.30 (s, br, 1H), 5.20 (s, 1H), 4.69 (s, 2H), 3.44-3.34 (m, 2H), 3.40 (s, 6H), 3.22-3.15 (m, 2H), 3.24 (s, 2H), 2.71-2.64 (m, 2H), 2.58-2.50 (m, 2H), 2.31 (s, 3H), 1.98-1.82 (m, 2H). (UPLC-MS 6) $t_R$ 0.33; ESI-MS 335.3 [M+H]⁺.

Step 8: 4-fluoro-5-iodopyridin-2-amine

A suspension of 4-fluoropyridin-2-amine (336 g, 2.5 mol) and NIS (745 g, 2.75 mol) in MeCN (9 L) was treated with TFA (114 g, 1 mol). The reaction mixture was then stirred at room temperature for 8 h. The reaction mixture was diluted with EtOAc (10 L), washed with sat. aq. Na₂S₂O₃ (2×5 L), brine (4×5 L). The combined organic layers were dried over Na₂SO₄, filtered and concentrated to get the crude product. The crude product was purified by recrystallization from EtOAc/pentane (1/10) to afford the title compound as a white solid. ¹H NMR (400 MHz, DMSO-d₆) δ 8.14 (d, 1H), 6.45 (s, 2H), 6.33 (d, 1H).

Step 9: 6-amino-4-fluoronicotinonitrile 4-fluoro-5-iodopyridin-2-amine (obtained in step 8, 240 g, 1 mol), zinc cyanide (125 g, 1.05 mol), zinc (13 g, 0.2 mol), Pd₂(dba)₃ (25 g, 25 mmol) and dppf (55 g, 0.1 mol) in DMA (800 mL) were degassed and charged into the round bottom flask under nitrogen. The mixture was stirred at 100° C. for 3 h. The reaction mixture was diluted with 5% NaHCO₃ (2 L), extracted with EtOAc (4×600 mL). The combined organic layers were washed with 5% NaOH (1 L), dried over Na₂SO₄, concentrated to 700 mL. The resulting organic phase was eluted through silica gel column with EtOAc (1.7 L). The combined organic filtrate was washed with 2 M HCl (3×800 mL). The pH of the aqueous phase was adjusted to 10 with saturated NaHCO₃. The aqueous phase was extracted whit DCM (3×500 mL). The combined DCM was dried over Na₂SO₄ and concentrated. The residue was further purified by column chromatography (eluted with pentane: EtOAc 10:1 to 3:2) followed by recrystallization from pentane/EtOAc 3/1 to give the title compound as white solid. ¹H NMR (400 MHz, DMSO-d₆) δ 8.40 (d, 1H), 7.40 (s, 2H), 6.34 (d, 1H).

Step 10: tert-butyl (4-chloro-5-cyanopyridin-2-yl)carbamate

A mixture of 2,4-dichloro-5-cyanopyridine (10 g, 57.8 mmol), tert-butyl carbamate (8.2 g, 70.5 mmol), Pd(OAc)₂ (0.26 g, 1.1 mmol), Xantphos (1.34 g, 2.3 mmol) and K₂CO₃ (12 g, 87 mmol) in THF (150 mL) was degassed 3× with nitrogen. The mixture was then heated at 70° C. for 4-5 h and monitored by chromatography until complete conversion. Following completion of the reaction, additional THF (100 mL) was added and heated the mixture at 70° C. for additional 1 h and then cooled to room temperature. The suspension was then filtered through a pad of celite to remove the solid. The filtrate was then concentrated and azotropically distilled with ethyl acetate before filtering to give the title compound. ¹H NMR (DMSO-d₆, 400 MHz): δ 10.82 (s, 1H), 8.79 (s, 1H), 8.09 (s, 1H), 1.49 (s, 9H).

Step 11: tert-butyl N-(5-cyano-4-((2-methoxyethyl) amino)pyridin-2-yl)carbamate

A mixture of tert-butyl (4-chloro-5-cyanopyridin-2-yl) carbamate (obtained in step 10, 9.8 g, 38.6 mmol), 2-methoxyethylamine (5.8 g, 77.3 mmol) and DIPEA (6 g, 46.4 mmol) in DMSO (80 mL) was heated at 65-70° C. for 24 h and monitored by chromatography until complete conversion. The solution was then cooled to room temperature and a white solid precipitated gradually. Water (20 mL) was then added slowly within 1 h. The suspension was stirred for a further 1 h, filtered and dried to give the title compound as a white solid. $^1$H NMR (DMSO-d$_6$, 400 MHz): δ 9.87 (s, 1H), 8.18 (s, 1H), 7.20 (s, 1H), 6.86 (s, 9H), 3.51 (t, 2H), 3.36 (t, 2H), 3.28 (s, 3H), 1.47 (s, 9H).

Step 12:
6-amino-4-((2-methoxyethyl)amino)nicotinonitrile

A solution of 6-amino-4-fluoronicotinonitrile (obtained in step 9, 1.10 g, 8.02 mmol) in DMA (20 mL) was treated with 2-methoxyethylamine (2.07 mL, 24.1 mmol) and DIPEA (4.20 mL, 24.1 mmol), heated to 50° C. and stirred for 15 h. The reaction mixture was cooled to room temperature and concentrated. The crude material was purified by normal phase chromatography (24 g silica gel cartridge, heptanes/EtOAc 100:0 to 0:100). The product containing fractions were concentrated and dried under vacuum to give the title compound as an off-white solid.
An alternative synthesis of 6-amino-4-((2-methoxyethyl) amino)nicotinonitrile is outlined below: To tert-butyl N-{5-cyano-4-[(2-methoxyethyl)amino]pyridin-2-yl}carbamate (obtained in step 11, 7 g) was added 30-36% aqueous HCl (40 mL), the mixture stirred at room temperature for 30 minutes and monitored by chromatography until complete conversion. The solution was then basified with 20-30% NaOH solution to pH=9-10 and filtered to give a white solid. The solid was added to ethyl acetate (15 mL) and heated to 50-55° C. to form a clear solution. The solution was then cooled to 3-6° C., stirred for 2-3 h and filtered. The wet cake was then dried to give the title compound as a white solid. $^1$H NMR (400 MHz, DMSO-d$_6$) δ 7.92 (s, 1H), 6.39 (s, 2H), 6.15 (t, 1H), 5.61 (s, 1H), 3.46 (t, 2H), 3.27 (s, 3H), 3.24 (q, 2H). (UPLC-MS 3) $t_R$ 0.62; ESI-MS 193.1 [M+H]$^+$.

Step 13: N-(5-cyano-4-((2-methoxyethyl)amino) pyridin-2-yl)-7-(dimethoxymethyl)-6-((4-methyl-2-oxopiperazin-1-yl)methyl)-3,4-dihydro-1,8-naphthyridine-1(2H)-carboxamide A solution of 6-amino-4-((2-methoxyethyl)amino)nicotinonitrile (obtained in step 12, 481 mg, 2.50 mmol) in anhydrous DMF (1.5 mL) was added drop wise over 10 minutes to a mixture of di(1H-1,2,4-triazol-1-yl)methanone (410 mg, 2.50 mmol) and DMF (1.5 mL) cooled at 0° C. After stirring for 45 minutes at 0° C. the reaction mixture was allowed to warm to room temperature and after a further 90 minutes at room temperature a solution of 1-((2-(dimethoxymethyl)-5,6,7,8-tetrahydro-1,8-naphthyridin-3-yl) methyl)-4-methylpiperazin-2-one (obtained in step 7, 418 mg, 1.00 mmol) in DMF (2 mL) was added. The reaction mixture was stirred for 17.5 h at room temperature, quenched by the addition of MeOH and evaporated. The residue was applied to a 80 g RediSep® silica column as a DCM solution and purified by normal phase chromatography, eluting with a gradient from DCM to 2% MeOH in DCM. Product containing fractions were combined and evaporated to give the title compound as an orange foam. $^1$H NMR (400 MHz, DMSO-d$_6$) δ 13.50 (s, 1H), 8.27 (s, 1H), 7.52 (s, 1H), 7.39 (s, 1H), 6.93 (t, 1H), 5.45 (s, 1H), 4.65 (s, 2H), 3.94-3.89 (m, 2H), 3.54-3.50 (m, 2H), 3.40-3.35 (m, 2H), 3.38 (s, 6H), 3.29 (s, 3H), 3.20-3.16 (m, 2H), 3.05 (s, 2H), 2.86-2.80 (m, 2H), 2.61-2.55 (m, 2H), 2.22 (s, 3H), 1.94-1.88 (m, 2H). (UPLC-MS 6) $t_R$ 0.72; ESI-MS 553.3 [M+H]$^+$.

Step 14: N-(5-cyano-4-((2-methoxyethyl)amino) pyridin-2-yl)-7-formyl-6-((4-methyl-2-oxopiperazin-1-yl)methyl)-3,4-dihydro-1,8-naphthyridine-1(2H)-carboxamide Concentrated hydrochloric acid (0.40 mL) was added to a solution of N-(5-cyano-4-((2-methoxyethyl)amino)pyridin-2-yl)-7-(dimethoxymethyl)-6-((4-methyl-2-oxopiperazin-1-yl)methyl)-3,4-dihydro-1,8-naphthyridine-1(2H)-carboxamide (obtained in step 13, 470 mg, 0.808 mmol) in THF (3 mL) and water (1 mL) at room temperature. After stirring for 3 h at room temperature saturated aqueous NaHCO$_3$ was added, the mixture extracted with DCM (3×), the organic layers dried over Na$_2$SO$_4$ and evaporated. The residue was sonicated with EtOAc (6 mL) and pentane (6 mL) and then filtered. The white solid obtained was then dissolved in DCM (6 mL), EtOAc added (3 mL), the solution warmed, sealed and allowed to stand at room temperature for 2 h. Filtration and drying gave N-(5-cyano-4-((2-methoxyethyl) amino)pyridin-2-yl)-7-formyl-6-((4-methyl-2-oxopiperazin-1-yl)methyl)-3,4-dihydro-1,8-naphthyridine-1(2H)-carboxamide as a white solid.
$^1$H NMR (400 MHz, DMSO-d$_6$) δ 13.43 (s, 1H), 10.06 (s, 1H), 8.24 (s, 1H), 7.49 (s, 1H), 7.47 (s, 1H), 6.96 (t, br, 1H), 4.86 (s, 2H), 3.96-3.90 (m, 2H), 3.52-3.46 (m, 2H), 3.39-3.33 (m, 2H), 3.30-3.21 (m, 2H), 3.37 (s, 3H), 3.02 (s, 2H), 2.93-2.86 (m, 2H), 2.61-2.56 (m, 2H), 2.21 (s, 3H), 1.95-1.85 (m, 2H). (UPLC-MS 6) $t_R$ 0.70, ESI-MS 507.2, [M+H]$^+$.

Step 15: N-(5-cyano-4-((2-methoxyethyl)amino) pyridin-2-yl)-7-formyl-6-((4-methyl-2-oxopiperazin-1-yl)methyl)-3,4-dihydro-1,8-naphthyridine-1(2H)-carboxamide in citric acid form (1:1)

N-(5-cyano-4-((2-methoxyethyl)amino)pyridin-2-yl)-7-formyl-6-((4-methyl-2-oxopiperazin-1-yl)methyl)-3,4-dihydro-1,8-naphthyridine-1(2H)-carboxamide (obtained in step 14, 4 g, 7.896 mmol) was stirred in propionic acid (29.3 g, 29.60 mL) at 70° C. until dissolution was complete (20 minutes). The solution was cooled to 55° C. and a solution of citric acid in acetone (23% w/w) was added to it. Separately, a seed suspension was prepared by adding acetone (0.2 g, 0.252 mL) to N-(5-cyano-4-((2-methoxyethyl)amino)pyridin-2-yl)-7-formyl-6-((4-methyl-2-oxopiperazin-1-yl)methyl)-3,4-dihydro-1,8-naphthyridine-1(2H)-carboxamide in citric acid form (0.0185 g, 0.026 mmol). The seed suspension was added to the solution at 50° C. and the resulting suspension was left to stir at 50° C. for 40 minutes. A further solution of citric acid in acetone (26.6 g, 2.51% w/w, 33.63 mL) was added to the reaction over 380 minutes. The resulting suspension was stirred for a further 120 minutes and cooled to 20° C. with stirring over 4 hours. The suspension was stirred for another 12 hours before filtering the suspension under vacuum and washing the resulting solid with a propionic acid: acetone solution (1:1, 7 g, 7.96 mL) at room temperature. The solid was further washed with acetone (7 g, 8.85 mL) at room temperature. The resulting solid was dried in an oven at 40° C. and 5 mbar to give the title compound as a light orange solid (5.2 g, 7.443 mmol). (mw 698.70), mp (DSC) 168.8° C. (onset).
XRPD analysis showed the same pattern as with particles obtained by a process described in PCT/IB2014/065585 (reference example 1)—see FIG. 5.

Example 1a

Steps 1 to 14 were carried out as described in example 1.

Step 15a: N-(5-cyano-4-((2-methoxyethyl)amino) pyridin-2-yl)-7-formyl-6-((4-methyl-2-oxopiperazin-1-yl)methyl)-3,4-dihydro-1,8-naphthyridine-1(2H)-carboxamide in citric acid form (1:1)

N-(5-cyano-4-((2-methoxyethyl)amino)pyridin-2-yl)-7-formyl-6-((4-methyl-2-oxopiperazin-1-yl)methyl)-3,4-dihydro-1,8-naphthyridine-1(2H)-carboxamide (obtained in step 14, 5 g, 9.930 mmol) was stirred in propionic acid (33.5 g, 33.84 mL) at 60° C. Once N-(5-cyano-4-((2-methoxyethyl)amino)pyridin-2-yl)-7-formyl-6-((4-methyl-2-oxopiperazin-1-yl)methyl)-3,4-dihydro-1,8-naphthyridine-1(2H)-carboxamide had dissolved, anhydrous citric acid powder (0.19 g, 0.9889 mmol) was added. The resulting suspension was heated to 70° C. and sonicated for 5 minutes to ensure full dissolution. The resulting solution was cooled to 50° C. and a solution of citric acid in ethyl acetate (3.7 g, 1.3% citric acid in ethyl acetate) was added over 20 minutes. Seeds of N-(5-cyano-4-((2-methoxyethyl)amino)pyridin-2-yl)-7-formyl-6-((4-methyl-2-oxopiperazin-1-yl)methyl)-3,4-dihydro-1,8-naphthyridine-1(2H)-carboxamide in citric acid form (0.02 g) were added to the solution and the suspension was aged for 15 minutes. Another aliquot of citric acid in ethyl acetate (128 g, 1.3% citric acid in ethyl acetate) was added to the suspension over 11.85 hours. The suspension was left to stir for over 4 hours. The suspension was then filtered under vacuum (500 mbar) and the resulting solid was washed firstly with a propionic acid: ethyl acetate solution (1:1, 7 g, 7.44 mL) at room temperature and then with ethyl acetate (12 g, 13.38 mL) at room temperature. The resulting solid was dried in an oven at 40° C. and 5 mbar to give the title compound as a light orange solid (6.3 g, 9.074 mmol).

XRPD analysis showed the same pattern as with particles obtained by a process described in PCT/IB2014/065585 (reference example 1)—see FIG. 5.

Reference Example 1 (Described in PCT/IB2014/065585)—N-(5-cyano-4-((2-methoxyethyl)amino)pyridin-2-yl)-7-formyl-6-((4-methyl-2-oxopiperazin-1-yl)methyl)-3,4-dihydro-1,8-naphthyridine-1(2H)-carboxamide in citric acid form (1:1)

Steps 1 to 14 were carried out as described in example 1.

Reference Step 15—N-(5-cyano-4-((2-methoxyethyl)amino)pyridin-2-yl)-7-formyl-6-((4-methyl-2-oxopiperazin-1-yl)methyl)-3,4-dihydro-1,8-naphthyridine-1(2H)-carboxamide in citric acid form (1:1)

A solution of citric acid (96.9 mg) in acetone (5 mL) was prepared at room temperature (0.1 M). A portion of the 0.1 M citric acid in acetone solution (2 mL) was then added to a suspension of N-(5-cyano-4-((2-methoxyethyl)amino)pyridin-2-yl)-7-formyl-6-((4-methyl-2-oxopiperazin-1-yl)methyl)-3,4-dihydro-1,8-naphthyridine-1(2H)-carboxamide (100 mg) in acetone (4 mL) and the mixture sonicated for 1 minute then heated at 55° C. with stirring for 2 h before slowly cooling to room temperature. The white solid was then collected by filtration, washing 2× with acetone (2 mL), and dried for 18 h at 40° C. under vacuum to give the title salt.

Alternatively, N-(5-cyano-4-((2-methoxyethyl)amino)pyridin-2-yl)-7-formyl-6-((4-methyl-2-oxopiperazin-1-yl)methyl)-3,4-dihydro-1,8-naphthyridine-1(2H)-carboxamide (6.5 g, 12.83 mmol) was placed in a 500 ml 4-flask reactor. 49 mL of glacial acetic acid was added and the resulting suspension was stirred at 23° C. until a clear mixture was obtained. In a separate flask, anhydrous 2-hydroxypropane-1,2,3-tricarboxylic acid (2.59 g, 13.47 mmol, 1.05 equiv.) was dissolved in 49 mL of glacial acetic acid at 50° C. until a clear solution was obtained. This solution was then added at 23° C. to the N-(5-cyano-4-((2-methoxyethyl)amino)pyridin-2-yl)-7-formyl-6-((4-methyl-2-oxopiperazin-1-yl) methyl)-3,4-dihydro-1,8-naphthyridine-1(2H)-carboxamide solution previously prepared. This mixture was stirred for 30 min at 23° C. and then added dropwise over 1 h to 192 mL of ethyl acetate warmed to 75° C. The temperature remained constant over the addition. At the end of the addition, the temperature of the mixture was cooled slowly to 23° C. and let 16 h at this temperature under gentle stirring. The suspension was cooled to 5-10° C. and filtered. The cake was washed with 15 mL of ethyl acetate and 15 mL of acetone. The wet cake (ca 8.5 g) was transferred in a 500 mL flask containing 192 mL of dry acetone. The resulting suspension was refluxed for 24 h. The suspension was filtered and the cake was washed with 2 times 15 mL of dry acetone then dried at 50° C. under vacuum for several hours to give the title salt.

Ex. 2—In-Vitro Biochemical Kinase Assays for FGFR4

All assays were performed in 384 well microtiter plates. Each assay plate contained 8-point serial dilutions for 40 test compounds, as well as four 8-point serial dilutions of staurosporine as reference compound, plus 16 high and 16 low controls.

Liquid handling and incubation steps were done on an Innovadyne Nanodrop Express equipped with a robotic arm (Thermo CatX, Caliper Twister II) and an incubator (Liconic STX40, Thermo Cytomat 2C450). The assay plates were prepared by addition of 50 nl per well of compound solution in 90% DMSO. The kinase reactions were started by stepwise addition of 4.5 µl per well of peptide/ATP-solution (50 mM HEPES, pH 7.5, 1 mM DTT, 0.02% Tween20, 0.02% BSA, 0.6% DMSO, 10 mM beta-glycerophosphate, and 10 µM sodium orthovanadate, 16 mM MgCl2, 1122 µM ATP, 4 µM peptide (5-Fluo-Ahx-KKKKEEIYFFFG-NH2, Biosyntan GmbH) and 4.5 µl per well of enzyme solution (50 mM HEPES, pH 7.5, 1 mM DTT, 0.02% Tween20, 0.02% BSA, 0.6% DMSO, 10 mM beta-glycerophosphate, and 10 µM sodium orthovanadate, 16 mM MgCl2, 6 nM FGFR4 (GST-FGFR4(388-802), produced in-house by expression in insect cells and affinity chromatography). Kinase reactions were incubated at 30° C. for 60 minutes and subsequently terminated by addition of 16 µl per well of stop solution (100 mM HEPES pH 7.5, 5% DMSO, 0.1% Caliper coating reagent, 10 mM EDTA, and 0.015% Brij35). Plates with terminated kinase reactions were transferred to the Caliper LC3000 workstations for reading. Phosphorylated and unphosphorylated peptides were separated using the Caliper microfluidic mobility shift technology. Briefly, samples from terminated kinase reactions were applied to the chip. Analytes are transported through the chip by constant buffer flow and the migration of the substrate peptide is monitored by the fluorescence signal of its label. Phosphorylated peptide (product) and unphosphorylated peptide (substrate) are separated in an electric field by their charge/mass ratio. Kinase activities were calculated from the amounts of formed phospho-peptide. IC50 values were determined from percent inhibition values at different compound concentrations by non-linear regression analysis.

Preparation of Compound Dilutions

Test compounds were dissolved in DMSO (10 mM) and transferred into 1.4 mL flat bottom or V-shaped Matrix tubes carrying a unique 2D matrix. The stock solutions were stored at +2° C. if not used immediately. For the test procedure the vials were defrosted and identified by a scanner whereby a working sheet was generated that guided the subsequent working steps.

Compound dilutions were made in 96 well plates. This format enabled the assay of maximally 40 individual test compounds at 8 concentrations (single points) including 4 reference compounds. The dilution protocol included the production of "pre-dilution plates", "master plates" and "assay plates".

Pre-Dilution Plates:

96 polypropylene well plates were used as pre-dilution plates. A total of 4 pre-dilution plates were prepared including 10 test compounds each on the plate positions A1-A10, one standard compound at A11 and one DMSO control at A12. All dilution steps were done on a HamiltonSTAR robot.

Master Plates:

30 µL of individual compound dilutions including standard compound and controls of the 4 "pre-dilution plates" were transferred into a 384 "master plate" including the following concentrations 1'810, 362, 72.5, 54.6, 14.5, 2.9, 0.58 and 0.12 µM, respectively in 90% of DMSO.

Assay Plates:

Identical "assay plates" were then prepared by pipetting 50 nL each of compound dilutions of the "master plates" into 384-well "assay plates" by means of a HummingBird 384-channel dispenser. These plates were used directly for the assay which was performed in a total volume of 9.05 µL. This led to a final compound concentration of 10, 2.0, 0.4, 0.08, 0.016, 0.0032, 0.00064 and 0.000128 µM and a final DMSO concentration of 0.5% in the assay.

In Vitro Cellular Kinase Assays for FGFR4

As a read out for cellular FGFR4 kinase activity, an assay that measures the Tyrosine phosphorylation content on FGFR4 was developed. For this, a BaF3-Tel-FGFR4 cell line was generated: BaF3 cells were stably transduced with a retrovirus encoding a fusion protein consisting of the amino terminal portion of TEL (aa1-337) fused to the cytoplasmic domain of FGFR4, including the juxtamembrane domain. The presence of the TEL domain mediates constitutive activation of the fused FGFR4 kinase by oligomerization, and thus autophosphorylation on the Tyrosine sites.

A MSD (Meso Scale Discovery)-based capture ELISA was developed and used as follows:

Cell treatment: 250000 BaF3-Tel-FGFR4 cells per well were seeded in 96-well tissue culture plates (Corning Cat#3359) in 40 uL of growth medium (RPMI-1640 (Amimed Cat#1-41F01-I) supplemented with 10% foetal calf serum, 10 mM HEPES, 1 mM Sodium Pyruvate, 2 mM Stable Glutamine and 1× Penicillin-Streptomycin). Using a liquid handling device (Velocity 11 Bravo, Agilent), serial 3-fold dilutions of compounds were prepared in DMSO, prediluted in growth medium, followed by transfer of 10 uL/well to the cell plates. After incubation for 1 hour at 37° C./5% CO2, 50 uL of lysis buffer (150 mM NaCl, 20 mM Tris (pH 7.5), 1 mM EDTA, 1 mM EGTA, 1% Triton X-100, 10 mM NaF, complemented with protease inhibitors (Complete Mini, Roche Cat#11836153001) and phosphatase) inhibitors (Phosphatase Inhib I, SIGMA Cat# P2850; Phosphatase Inhib II, SIGMA Cat# P5726 according to supplier instructions) was added and incubated for 30 minutes on ice with shaking at 300 rpm. Sample plates were then frozen and stored at −70° C. Following thawing on ice, the sample plates were centrifuged for 15 minutes at 1200 rpm at 6° C.

ELISA assay: Multi array 96 well plates (MSD, Cat# L15XB-3) were coated for 1 hour at room temperature with 25 uL/well of mouse anti-H-TEL antibody (Santa Cruz, Cat#sc-166835) diluted 1:400 in PBS/O. Following addition of 150 uL of 3% MSD-blocker A (Cat# R93BA-1) in TBS-T (50 mM Tris, 150 mM NaCl, 0.02% Tween-20), plates were incubated for 1 hour at room temperature with shaking. Plates were then washed 3 times with 200 uL/well of TBS-T. 50 uL of the cell lysate was then transferred to the coated plate and incubated for 15 hours at 4° C., followed by 3 washes with 200 µl TBS-T/well and addition of 25 µl/well of MSD SULFOTAGGED PY20 antibody (MSD Cat# R32AP-5), diluted 1:250 in TBS-T+1% MSD Blocker A. Following Incubation for 1 h at room temperature with shaking, wells were washed 3 times with 200 µl TBS-T/well. Following ition of 150 µl MSD Read Buffer (MSD, Cat# R92TC-2) stock solution diluted 1:4 with nano water, electro-chemiluminescent signal generation was immediately quantified on a SectorImager 6000 (MSD), IC50 calculation: For data analysis, the assay background was determined in wells containing medium and lysis buffer, but no cells, and the corresponding value subtracted from all data points. The effect of a particular test compound concentration on FGFR4 phosphorylation is expressed as percentage of the background-corrected electro-chemiluminescence reading obtained for cells treated with vehicle only (DMSO, 0.2% f.c.), which is set as 100. Compound concentrations leading to half-maximal signal inhibition (1050) were determined by standard four parametric curve fitting (XLfit 5.4, IDBS).

Cell Proliferation Assay

Methylene Blue Staining Proliferation Assay (MBS):

The effect of compounds on cell proliferation is assessed using HuH-7 hepatocellular carcinoma cells obtained from the Japanese Collection of Research Bioresources Cell Bank (Cat# JCRB0403) and cultured in the vendor-recommended medium (DMEM high glucose (Amimed Cat#1-26F01-I), 10% foetal calf serum (Invitrogen Cat#16140-071), 1 mM sodium pyruvate (Amimed Cat#5-60F00-H), 1× Penicillin/Streptomycin (Amimed Cat#4-01F00-H)) at 37° C. in a humidified 5% CO2 incubator. Specifically, 5000 cells/well were seeded in 96-well tissue culture plates (TPP Cat#92696) in a total media volume of 100 µl/well and increasing compound dilutions or DMSO were added 24 hours thereafter in triplicates. 72 hours after compound addition, cells were fixed by adding 25 µL/well of 20% glutaraldehyde (Sigma Aldrich Cat# G400-4) and incubated for 10 minutes at room temperature. Cells were washed three times with $H_2O$, 200 µL/well and stained with 100 µL/well 0.05% methylene blue (ABCR GmbH Cat# AB117904) for 10 minutes at room temperature. Cells were washed 3 times with H2O, 200 µL/well and then lysed by adding 200 µL/well of 3% HCl (Fluka Cat#84422) for 30 minutes at room temperature with shaking. Optical density was measured at A650 nm. The concentration of compound providing 50% of proliferation inhibition with respect to DMSO-treated cells was determined ($IC_{50}$) using XLFit software.

CellTiter Glo (CTG) Assay:

The functional effect of compounds on cell proliferation is assessed using HuH-7 hepatocellular carcinoma cells obtained from the Japanese Collection of Research Bioresources Cell Bank (Cat# JCRB0403) and cultured in the vendor-recommended medium (DMEM high glucose (Amimed Cat#1-26F01-I), 10% foetal calf serum (Invitrogen Cat#16140-071), 1 mM sodium pyruvate (Amimed Cat#5-60F00-H), 1× Penicillin/Streptomycin (Amimed Cat#4-01F00-H)) at 37° C. in a humidified 5% CO2 incubator. Compound-mediated suppression of cell proliferation/ viability is assessed by quantification of cellular ATP levels using the CellTiter-Glo (CTG) reagent (Promega, Cat# G7573). Briefly, cells are seeded at 3'000 cells/well/80 μl fresh medium into tissue-culture-treated 96-well plates (Costar Cat#3904), followed by addition of 20 μl medium containing compound dilutions at 5-fold their final intended concentration. Dose-response effects are assessed by 3-fold serial dilutions of the test compound, starting at 10 μM. Following incubation of the cells for 3 days at 37° C. and 5% $CO_2$, the effect of inhibitors on cell viability is quantified following addition of 50 μl CTG and luminescence measurement (integration time: 500 ms) as per vendor manual, using a correspondingly equipped multi-mode plate reader (M200Pro, TECAN, Switzerland). For data analysis, the assay background value determined in wells containing medium, but no cells, is subtracted from all data points. To enable differentiation of cytotoxic from cytostatic compounds, the number of viable cells is assessed relative to that observed at the time of compound addition using a separate cell plate (day 0). The effect of a particular test compound concentration on cell proliferation/viability is expressed as percentage of the background- and day 0-corrected luminescence reading obtained for cells treated with vehicle only (DMSO, 0.1% f.c.), which is set as 100%, whereas the luminescence reading for wells containing medium only, but no cells, is set as −100%. Compound concentrations leading to half-maximal growth inhibition (GI50) are determined using standard four parameter curve fitting (XLfit 5.2, IDBS, UK).

| Example | Biochemical FGFR4 $IC_{50}$ (nM) | Cellular BaF$_3$ FGFR4 $IC_{50}$ (nM) | HUH7 proliferation (nM) | |
|---|---|---|---|---|
| | | | MBS | CTG |
| 1 | 1.9 | 4.3 | 12 | 60.9 |

Comparative Data

In vitro biochemical assays for FGFR1 (407-822), FGFR2 (406-821) and FGFR3 (411-806) were conducted in a similar manner to the in vitro biochemical assay for FGFR4 described above, using the indicated portions of the kinase domains. Example 1 produced $IC_{50}$ values >10000 nM in the biochemical FGFR1, FGFR2 and FGFR3 assays.

Example 3—Laser diffraction measurement of particles of N-(5-cyano-4-((2-methoxyethyl)amino) pyridin-2-yl)-7-formyl-6-((4-methyl-2-oxopiperazin-1-yl)methyl)-3,4-dihydro-1,8-naphthyridine-1(2H)-carboxamide obtained in example 1

The particle size distribution of N-(5-cyano-4-((2-methoxyethyl)amino)pyridin-2-yl)-7-formyl-6-((4-methyl-2-oxopiperazin-1-yl)methyl)-3,4-dihydro-1,8-naphthyridine-1(2H)-carboxamide in citric acid form (1:1) obtained in example 1 was analyzed according to the method described in the European Pharmacopoeia chapter 2.9.31 Particle size analysis by laser light diffraction.

For the measurement, a Sympatec HELOS device with a focal length of 500 mm from Sympatec GmbH, Germany, equipped with a wet dispersion device Cuvette from Sympatec GmbH, Germany was used. The test substance was dispersed in white spirit, Brenntag Schweizerhall AG, Switzerland (catalog number 12200-150) using a dispersing aid (e.g. Statsafe™ 6000, INNOSPEC Limited, ca. 1% in the white spirit).

Procedure:

Drops of the dispersing aid were added under manual mixing to the powder sample of N-(5-cyano-4-((2-methoxyethyl)amino)pyridin-2-yl)-7-formyl-6-((4-methyl-2-oxopiperazin-1-yl)methyl)-3,4-dihydro-1,8-naphthyridine-1(2H)-carboxamide in citric acid form (1:1) obtained in example 1. The particles were mixed intensively, e.g. on a vortex mixer, in order to wet the substance thoroughly and to form a smooth and homogeneous paste. The paste was diluted with the white spirit to a final volume of several milliliters and the stock dispersion was mixed again.

Measurement:

The test dispersion was prepared by diluting of the stock dispersion with white spirit for an appropriate optical concentration and the cumulative volume distribution was determined using a laser light diffraction instrument in accordance with the instruction manual. Measurements were made before and after 10 seconds, 20 seconds, 30 seconds sonication. The parameters were set as follows: 30% amplitude and 80% cycle time at the ultrasonication device GM70 from Bandelin electronic GmbH & Co. KG, and a measuring duration of about 20 seconds.

The particle sizes at the undersize values of 10%, 50% and 90% (x10, x50, x90) were evaluated from the cumulative volume distribution without sonication. Sonication had no significant impact on the measured particles sizes.

The resulting particle size distribution is shown in FIG. 6.

Example 4—Laser diffraction measurement of particles of N-(5-cyano-4-((2-methoxyethyl)amino) pyridin-2-yl)-7-formyl-6-((4-methyl-2-oxopiperazin-1-yl)methyl)-3,4-dihydro-1,8-naphthyridine-1(2H)-carboxamide obtained in reference example 1 (described in PCT/IB2014/065585)

The particle size distribution of N-(5-cyano-4-((2-methoxyethyl)amino)pyridin-2-yl)-7-formyl-6-((4-methyl-2-oxopiperazin-1-yl)methyl)-3,4-dihydro-1,8-naphthyridine-1(2H)-carboxamide in citric acid form (1:1) obtained in reference example 1 was analyzed according to the method described in the European Pharmacopoeia chapter 2.9.31 Particle size analysis by laser light diffraction.

For the measurement, a Sympatec HELOS device with a focal length of 100 mm from Sympatec GmbH, Germany, equipped with a wet dispersion device Cuvette from Sympatec GmbH, Germany was used. The test substance was dispersed in white spirit, Brenntag Schweizerhall AG, Switzerland (catalog number 12200-150) using a dispersing aid (e.g. Statsafe™ 6000, INNOSPEC Limited, ca. 1% in the white spirit).

Procedure:

Drops of the dispersing aid were added under manual mixing to the powder sample of N-(5-cyano-4-((2-methoxyethyl)amino)pyridin-2-yl)-7-formyl-6-((4-methyl-2-oxopiperazin-1-yl)methyl)-3,4-dihydro-1,8-naphthyridine-1(2H)-carboxamide in citric acid salt form (1:1) obtained in example 1. The particles were mixed intensively, e.g. on a vortex mixer, in order to wet the substance thoroughly and to form a smooth and homogeneous paste. The paste was diluted with the white spirit to a final volume of several milliliters and the stock dispersion was mixed again.

Measurement:

The test dispersion was prepared by diluting of the stock dispersion with white spirit for an appropriate optical concentration and the cumulative volume distribution was determined using a laser light diffraction instrument in accordance with the instruction manual. Measurements were made before sonication and after sonication for up to 600 seconds. The parameters were set as follows: 50% amplitude at the ultrasonication device USGD-100 from Telsonic AG, and a measuring duration of about 20 seconds. The measurement was carried out twice.

The particle sizes at the undersize values of 10%, 50% and 90% (x10, x50, x90) were evaluated from the cumulative volume distribution after 240 seconds sonication. This was determined to be representative of the primary particle sizes.

Figure 7:
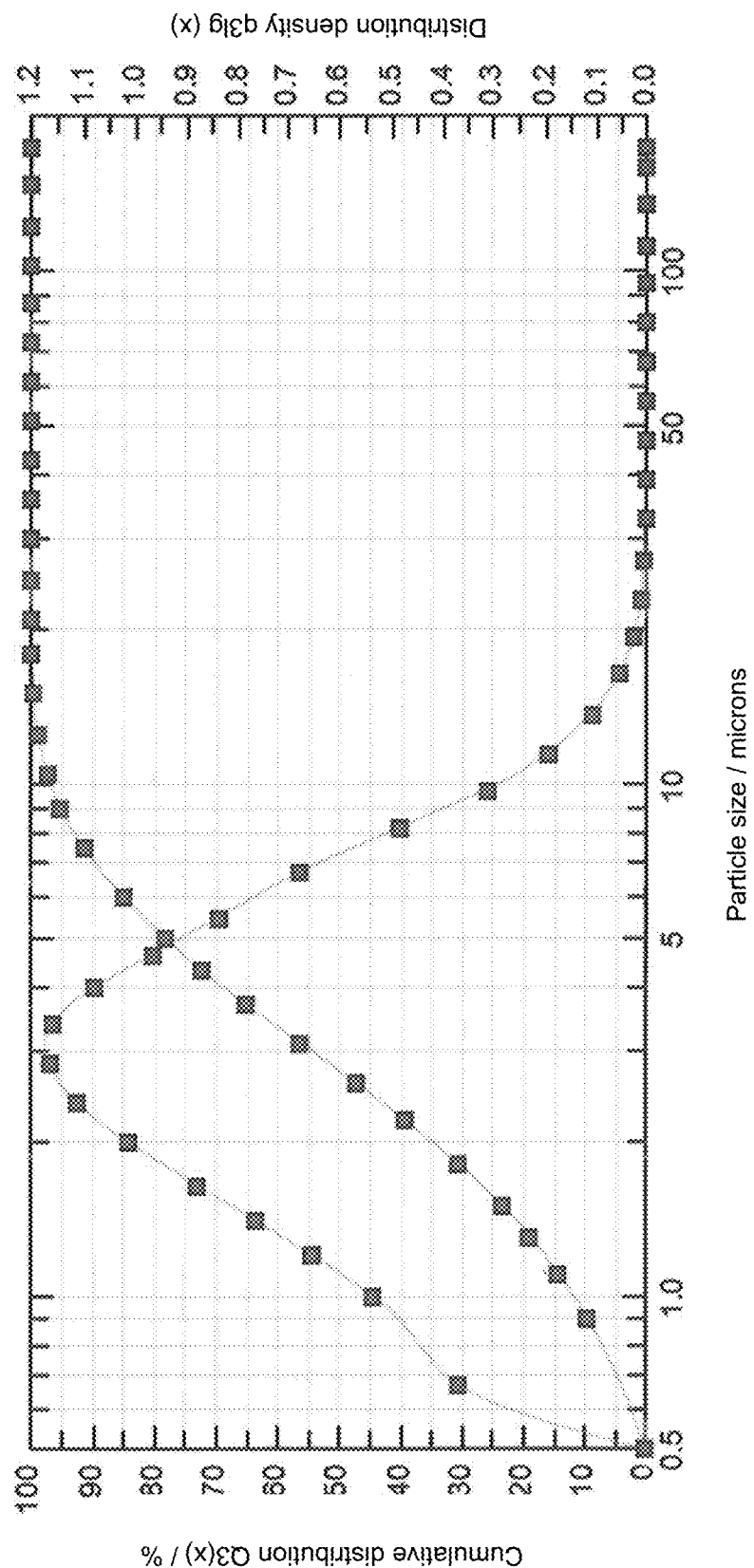
FIG. 7 shows the particle size distribution for particles obtained using the process described in PCT/IB2014/065585. The figure shows the distribution density and the cumulative distribution curves as a function of particle size. It shows that the particles have a particle size range from about 0.5 to 30 microns.

The resulting particle size distribution is shown in FIG. 7.

Example 5—Basic Flow Energy Measurements

Basic flow energy (BFE) is the energy required to establish a particular flow pattern in a conditioned, precise volume of powder. This flow pattern is a downward anti-clockwise motion of the blade, generating a compressive, relatively high stress flow mode in the powder. The BFE is calculated from the work done in moving the blade through the powder from the top of the vessel to the bottom, i.e. during the downward traverse.

In the present instance, the basic flow energy was measured using a FT4 powder rheometer from Freeman Technology under the following conditions: vessel size: 25 mm; standard Program Name: 25 mm_1C_Split_1 T; Starting accessory: 23.5 mm blade; Vessel: 25 mm×25 mL Split Vessel. The results were plotted in FIG. 9.

The basic flow energy measured for 2 samples of particles of the invention was 39.17 mJ for particles obtained by the process described in example 1a; and 65.07 mJ for particles obtained by the process described in example 1.

The basic flow energy measured for the samples of particles obtained by the process described in PCT/IB2014/065585 was 185.20 mJ.

These results suggest that the particles of the invention have improved flow properties over those of the particles obtained by the process described in PCT/IB2014/065585.

Example 6—Compressibility Measurements

Compressibility is a measure of how density changes as a function of applied normal stress. By definition, compressibility is the percent change in volume after compression (%). The measurements were made using a FT-4 powder rheometer from Freeman technology. N-(5-cyano-4-((2-methoxyethyl)amino)pyridin-2-yl)-7-formyl-6-((4-methyl-2-oxopiperazin-1-yl)methyl)-3,4-dihydro-1,8-naphthyridine-1(2H)-carboxamide particles obtained by the process of the present invention and particles obtained by the process described in PCT/IB2014/065585 were placed in a vessel and a vented piston was used to compress the particles. The vented piston is designed such that the compression face is constructed from a woven stainless steel mesh and allows the entrained air in the powder to escape uniformly across the surface of the powder bed. A normal stress was applied in 8 sequential compression steps beginning at 0.5 kPa and ending at 15 kPa. In each step, the normal stress was held constant for 60 seconds and the compressibility was automatically calculated as a percentage change in volume. The results were plotted in FIG. 10. The compressibility percentage measured at 15 kPa was 54.14% and 54.63% for particles of the present invention. For the particles obtained by the process described in PCT/IB2014/065585, the compressibility percentage measured at 15 kPa was 49.93%.

These results suggest that the particles of the invention are more compressible compared to those obtained by the process described in PCT/IB2014/065585, which would offer the advantage that higher drug load in the final drug product could be achieved by using the particles of the invention.

Example 7—Wall Friction Angle Measurements

The wall friction test method has been developed to assess the interaction between the drug substance and stainless steel. The apparatus used is a FT-4 powder rheometer from Freeman technology.

N-(5-cyano-4-((2-methoxyethyl)amino)pyridin-2-yl)-7-formyl-6-((4-methyl-2-oxopiperazin-1-yl)methyl)-3,4-dihydro-1,8-naphthyridine-1(2H)-carboxamide particles obtained by the process of the present invention and particles obtained by the process described in PCT/IB2014/065585 were placed in a vessel containing the sample and a wall friction head to induce both vertical and rotational stresses. The powder sample is prepared by conditioning and then pre-consolidation using the standard FT4 blade and vented piston.

The wall friction head equipped with 1.2 microns average roughness of 316 Stainless Steel discs moves downwards to the surface of the sample and induces a normal stress as the disc contacts the top of the sample. The head continues to move downwards until the required normal stress is established. Slow rotation of the wall friction head then begins, inducing a shear stress. A shear plane is established between the disc and sample surfaces. As the powder bed resists the rotation of the wall friction head, the torque increases until the resistance is eventually overcome. At this point, a maximum torque is observed. The wall friction head continues to rotate at 18 degrees/min for 5 minutes. The torque required to maintain this rotational is measured which enables a "steady-state" shear stress to be calculated. The normal stress is maintained constant at the target applied stress for each step throughout that step. A series of shear stress values is measured for a range of target applied stresses. Due to the nature of the samples and the fact that an exact constant rotational torque is unlikely to be achieved, the software determines an average value during 10% of the shearing time. The wall friction angle is then calculated by drawing a best fit line through the data points on the graph, and measuring the angle subtended between this best fit line and the horizontal. The results were plotted in FIG. 11.

The wall friction angle measured was 34.58° and 35.85° for particles of the present invention. For the particles obtained by the process described in PCT/IB2014/065585, the wall friction angle was 43.18°.

These results suggest that the particles of the invention exhibit less sticky behaviour to metal surfaces and have thus improved processability compared to those obtained by the process described in PCT/IB2014/065585.

The invention claimed is:

1. A process for the preparation of particles of N-(5-cyano-4-((2-methoxyethyl)amino)pyridin-2-yl)-7-formyl-6-((4-methyl-2-oxopiperazin-1-yl)methyl)-3,4-dihydro-1,8-naphthyridine-1(2H)-carboxamide in citric acid salt form comprising the steps of:
    a)—dissolving N-(5-cyano-4-((2-methoxyethyl)amino)pyridin-2-yl)-7-formyl-6-((4-methyl-2-oxopiperazin-1-yl)methyl)-3,4-dihydro-1,8-naphthyridine-1(2H)-carboxamide in propionic acid;

b)—adding citric acid to the solution obtained in step a) to obtain a suspension comprising N-(5-cyano-4-((2-methoxyethyl)amino)pyridin-2-yl)-7-formyl-6-((4-methyl-2-oxopiperazin-1-yl)methyl)-3,4-dihydro-1,8-naphthyridine-1(2H)-carboxamide in citric acid salt form; and c)—isolating the particles of N-(5-cyano-4-((2-methoxyethyl)amino)pyridin-2-yl)-7-formyl-6-((4-methyl-2-oxopiperazin-1-yl)methyl)-3,4-dihydro-1,8-naphthyridine-1(2H)-carboxamide in citric acid salt form from the suspension obtained in step b.

2. A process according to claim 1, which comprises after step b) a step of seeding the solution obtained in step b) with particles of N-(5-cyano-4-((2-methoxyethyl)amino)pyridin-2-yl)-7-formyl-6-((4-methyl-2-oxopiperazin-1-yl)methyl)-3,4-dihydro-1,8-naphthyridine-1(2H)-carboxamide in citric acid salt form to obtain a suspension comprising N-(5-cyano-4-((2-methoxyethyl)amino)pyridin-2-yl)-7-formyl-6-((4-methyl-2-oxopiperazin-1-yl)methyl)-3,4-dihydro-1,8-naphthyridine-1(2H)-carboxamide in citric acid salt form.

3. A process according to claim 1, wherein the citric acid added in step b) is added in aliquots.

4. A process according to claim 1, wherein the citric acid added in step b) is added as a solution and/or in solid form.

5. A process according to claim 4, wherein the citric acid is added as a solution of citric acid in a solvent selected from heptane, methyl tert-butyl ether, n-hexane, ethyl acetate, n-propyl acetate, acetone, acetonitrile, toluene and water or mixtures thereof.

6. Particles of N-(5-cyano-4-((2-methoxyethyl)amino)pyridin-2-yl)-7-formyl-6-((4-methyl-2-oxopiperazin-1-yl)methyl)-3,4-dihydro-1,8-naphthyridine-1(2H)-carboxamide in citric acid salt form obtainable by a process according to claim 1.

7. Particles of N-(5-cyano-4-((2-methoxyethyl)amino)pyridin-2-yl)-7-formyl-6-((4-methyl-2-oxopiperazin-1-yl)methyl)-3,4-dihydro-1,8-naphthyridine-1(2H)-carboxamide in citric acid salt form having a median particle size x50 of between 200 and 300 microns.

8. Particles of N-(5-cyano-4-((2-methoxyethyl)amino)pyridin-2-yl)-7-formyl-6-((4-methyl-2-oxopiperazin-1-yl)methyl)-3,4-dihydro-1,8-naphthyridine-1(2H)-carboxamide in citric acid salt form having a particle size x10 of between 5 and 10 microns.

9. Particles of N-(5-cyano-4-((2-methoxyethyl)amino)pyridin-2-yl)-7-formyl-6-((4-methyl-2-oxopiperazin-1-yl)methyl)-3,4-dihydro-1,8-naphthyridine-1(2H)-carboxamide in citric acid salt form having a particle size x90 of between 400 and 500 microns.

10. Primary particles of N-(5-cyano-4-((2-methoxyethyl)amino)pyridin-2-yl)-7-formyl-6-((4-methyl-2-oxopiperazin-1-yl)methyl)-3,4-dihydro-1,8-naphthyridine-1(2H)-carboxamide in citric acid salt form having a median particle size x50 of between 10 and 20 microns.

11. Crystalline primary particle of N-(5-cyano-4-((2-methoxyethyl)amino)pyridin-2-yl)-7-formyl-6-((4-methyl-2-oxopiperazin-1-yl)methyl)-3,4-dihydro-1,8-naphthyridine-1(2H)-carboxamide in citric acid salt form having a columnar crystal shape.

12. An agglomerate comprising primary particles of N-(5-cyano-4-((2-methoxyethyl)amino)pyridin-2-yl)-7-formyl-6-((4-methyl-2-oxopiperazin-1-yl)methyl)-3,4-dihydro-1,8-naphthyridine-1(2H)-carboxamide in citric acid salt form, wherein the primary particles of N-(5-cyano-4-((2-methoxyethyl)amino)pyridin-2-yl)-7-formyl-64(4-methyl-2-oxopiperazin-1-yl)methyl)-3,4-dihydro-1,8-naphthyridine-1(2H)-carboxamide in citric acid salt form are according to claim 10.

13. An agglomerate comprising primary particles of N-(5-cyano-4-((2-methoxyethyl)amino)pyridin-2-yl)-7-formyl-6-((4-methyl-2-oxopiperazin-1-yl)methyl)-3,4-dihydro-1,8-naphthyridine-1(2H)-carboxamide in citric acid salt form, the agglomerate having a median size x50 of between 300 and 400 microns.

14. A pharmaceutical composition comprising particles of N-(5-cyano-4-((2-methoxyethyl)amino)pyridin-2-yl)-7-formyl-6-((4-methyl-2-oxopiperazin-1-yl)methyl)-3,4-dihydro-1,8-naphthyridine-1(2H)-carboxamide in citric acid form according to claim 6 and optionally one or more pharmaceutically acceptable carriers.

15. A method of treating cancer selected from the group comprising liver cancer, breast cancer, glioblastoma, prostate cancer, rhabdomyosarcoma, gastric cancer, ovarian cancer, lung cancer and colon cancer with a pharmaceutical composition comprising N-(5-cyano-4-((2-methoxyethyl)amino)pyridin-2-yl)-7-formyl-6-((4-methyl-2-oxopiperazin-1-yl)methyl)-3,4-dihydro-1,8-naphthyridine-1(2H)-carboxamide in citric acid salt form.

* * * * *